US012773166B2

(12) United States Patent
Windmiller et al.

(10) Patent No.: US 12,773,166 B2
(45) **Date of Patent: *Oct. 27, 2026**

(54) HETEROGENEOUS INTEGRATION OF SILICON-FABRICATED SOLID MICRONEEDLE SENSORS AND CMOS CIRCUITRY

(71) Applicant: Biolinq Incorporated, San Diego, CA (US)

(72) Inventors: Joshua Windmiller, San Diego, CA (US); Jared Rylan Tangney, Encinitas, CA (US)

(73) Assignee: Biolinq Incorporated, San Diego, CA (US)

( * ) Notice: Subject to any disclaimer, the term of this patent is extended or adjusted under 35 U.S.C. 154(b) by 331 days.

This patent is subject to a terminal disclaimer.

(21) Appl. No.: 18/610,163

(22) Filed: Mar. 19, 2024

(65) Prior Publication Data

US 2024/0382157 A1 Nov. 21, 2024

Related U.S. Application Data

(63) Continuation of application No. 17/349,234, filed on Jun. 16, 2021, now Pat. No. 11,963,796, which is a (Continued)

(51) Int. Cl.
*A61B 5/00* (2006.01)
*A61M 37/00* (2006.01)

(52) U.S. Cl.
CPC ............ *A61B 5/685* (2013.01); *A61B 5/0048* (2013.01); *A61M 37/0015* (2013.01); *A61M 2037/0046* (2013.01)

(58) Field of Classification Search
CPC ....... A61B 5/685; A61B 5/1451; A61B 5/145; A61M 37/0015; A61M 2037/0046
See application file for complete search history.

(56) References Cited

U.S. PATENT DOCUMENTS 3,964,482 A 6/1976 Gerstel et al.
4,305,401 A 12/1981 Reissmueller et al.
(Continued)

FOREIGN PATENT DOCUMENTS

AU 2004200303 A1 2/2004
AU 2011202767 A1 6/2011
(Continued)

OTHER PUBLICATIONS

Al Hayek et al., "Patient Satisfaction and Clinical Efficacy of Novel Blood Glucose Meters Featuring Color Range Indicators in Patients With Type 2 Diabetes: A Prospective Study" Cureus Oct. 27, 2020; 12(10):e11195. 8 pages.
(Continued)

*Primary Examiner* — Eric J Messersmith
(74) *Attorney, Agent, or Firm* — Cooley LLP

(57) ABSTRACT

A skin-adorned physiological or biochemical sensing device is disclosed herein. The device preferably comprises a first substrate and a second substrate. The first substrate comprises an array of solid microneedles designed to penetrate a biological interface to access a physiological fluid or tissue. Each microneedle is capable of electrical interface with the physiological fluid or tissue. The second substrate comprises integrated circuitry designed to transduce at least one signal produced by an electrophysiological or electrochemical reaction. A sensing device is formed that is capable of interpreting the signal arising from the electrophysiological or electrochemical reaction to ascertain the level of some physiological or biochemical entity.

20 Claims, 4 Drawing Sheets

Related U.S. Application Data continuation of application No. 15/961,793, filed on Apr. 24, 2018, now Pat. No. 11,045,142.

(60) Provisional application No. 62/492,142, filed on Apr. 29, 2017.

(56) References Cited

U.S. PATENT DOCUMENTS

| | | | | |
|---|---|---|---|---|
| 4,323,996 | A | 4/1982 | Ganter | |
| 4,407,295 | A | 10/1983 | Steuer et al. | |
| 4,450,842 | A | 5/1984 | Zick et al. | |
| 4,908,117 | A | 3/1990 | Kinlen et al. | |
| 4,919,770 | A | 4/1990 | Preidel et al. | |
| 4,969,468 | A | 11/1990 | Byers et al. | |
| 5,035,711 | A | 7/1991 | Aoki et al. | |
| 5,131,390 | A | 7/1992 | Sakaguchi et al. | |
| 5,215,088 | A | 6/1993 | Normann et al. | |
| 5,279,543 | A | 1/1994 | Glikfeld et al. | |
| 5,286,364 | A | 2/1994 | Yacynych et al. | |
| 5,540,828 | A | 7/1996 | Yacynych | |
| 5,730,714 | A | 3/1998 | Guy et al. | |
| 5,766,132 | A | 6/1998 | Yasukawa et al. | |
| 5,832,410 | A | 11/1998 | Lin et al. | |
| 5,869,078 | A | 2/1999 | Baudino | |
| 5,953,306 | A | 9/1999 | Yi | |
| 6,036,055 | A | 3/2000 | Mogadam et al. | |
| 6,048,337 | A | 4/2000 | Svedman | |
| 6,091,975 | A | 7/2000 | Daddona et al. | |
| 6,104,940 | A | 8/2000 | Watanabe et al. | |
| 6,132,449 | A | 10/2000 | Lum et al. | |
| 6,132,499 | A | 10/2000 | Wong et al. | |
| 6,132,755 | A | 10/2000 | Eicher et al. | |
| 6,139,718 | A | 10/2000 | Kurnik et al. | |
| 6,175,752 | B1 | 1/2001 | Say et al. | |
| 6,269,053 | B1 | 7/2001 | Kawata et al. | |
| 6,284,126 | B1 | 9/2001 | Kurnik et al. | |
| 6,319,374 | B1 | 11/2001 | Nordling | |
| 6,364,890 | B1 | 4/2002 | Lum et al. | |
| 6,413,396 | B1 | 7/2002 | Yang et al. | |
| 6,432,723 | B1 | 8/2002 | Plaxco et al. | |
| 6,465,091 | B1 | 10/2002 | Ou-Yang | |
| 6,471,903 | B2 | 10/2002 | Sherman et al. | |
| 6,527,762 | B1 | 3/2003 | Santini, Jr. et al. | |
| 6,551,849 | B1 | 4/2003 | Kenney | |
| 6,587,705 | B1 | 7/2003 | Kim et al. | |
| 6,599,408 | B1 | 7/2003 | Chan et al. | |
| 6,603,987 | B2 | 8/2003 | Whitson | |
| 6,611,707 | B1 | 8/2003 | Prausnitz et al. | |
| 6,793,789 | B2 | 9/2004 | Choi et al. | |
| 6,801,041 | B2 | 10/2004 | Karinka et al. | |
| 6,814,845 | B2 | 11/2004 | Wilson et al. | |
| 6,862,466 | B2 | 3/2005 | Ackerman | |
| 6,908,453 | B2 | 6/2005 | Fleming et al. | |
| 7,081,195 | B2 | 7/2006 | Simpson et al. | |
| 7,097,776 | B2 | 8/2006 | Govinda Raju | |
| 7,132,054 | B1 | 11/2006 | Kravitz et al. | |
| 7,183,068 | B2 | 2/2007 | Burson et al. | |
| 7,262,068 | B2 | 8/2007 | Roy et al. | |
| 7,343,188 | B2 | 3/2008 | Sohrab | |
| 7,344,499 | B1 | 3/2008 | Prausnitz et al. | |
| 7,366,556 | B2 | 4/2008 | Brister et al. | |
| 7,415,299 | B2 | 8/2008 | Zimmermann et al. | |
| 7,429,333 | B2 | 9/2008 | Chiou et al. | |
| 7,456,112 | B2 | 11/2008 | Lee | |
| 7,471,972 | B2 | 12/2008 | Rhodes et al. | |
| 7,473,244 | B2 | 1/2009 | Frazier et al. | |
| 7,493,232 | B1 | 2/2009 | Surina | |
| 7,534,330 | B2 | 5/2009 | Yu et al. | |
| 7,583,990 | B2 | 9/2009 | Goode, Jr. et al. | |
| 7,599,726 | B2 | 10/2009 | Goode, Jr. et al. | |
| 7,613,491 | B2 | 11/2009 | Boock et al. | |
| 7,645,263 | B2 | 1/2010 | Angel et al. | |
| 7,715,893 | B2 | 5/2010 | Kamath et al. | |
| 7,725,148 | B2 | 5/2010 | Shah et al. | |
| 7,768,408 | B2 | 8/2010 | Reggiardo et al. | |

| | | | | |
|---|---|---|---|---|
| 7,778,680 | B2 | 8/2010 | Goode, Jr. et al. | |
| 7,785,301 | B2 | 8/2010 | Yuzhakov | |
| 7,797,028 | B2 | 9/2010 | Goode, Jr. et al. | |
| 7,811,231 | B2 | 10/2010 | Jin et al. | |
| 7,837,654 | B2 | 11/2010 | Shumate et al. | |
| 7,885,697 | B2 | 2/2011 | Brister et al. | |
| 7,905,833 | B2 | 3/2011 | Brister et al. | |
| 7,917,186 | B2 | 3/2011 | Kamath et al. | |
| 7,949,382 | B2 | 5/2011 | Jina | |
| 7,959,569 | B2 | 6/2011 | Goode et al. | |
| 8,005,526 | B2 | 8/2011 | Martin et al. | |
| 8,010,174 | B2 | 8/2011 | Goode, Jr. et al. | |
| 8,022,292 | B2 | 9/2011 | Arianpour et al. | |
| 8,064,977 | B2 | 11/2011 | Boock et al. | |
| 8,088,321 | B2 | 1/2012 | Ferguson et al. | |
| 8,094,009 | B2 | 1/2012 | Allen et al. | |
| 8,108,023 | B2 | 1/2012 | Mir et al. | |
| 8,110,079 | B2 | 2/2012 | Gooding et al. | |
| 8,125,331 | B2 | 2/2012 | Allen et al. | |
| 8,130,095 | B2 | 3/2012 | Allen et al. | |
| 8,160,665 | B2 | 4/2012 | Mischler et al. | |
| 8,160,671 | B2 | 4/2012 | Kamath et al. | |
| 8,160,834 | B2 | 4/2012 | Liang et al. | |
| 8,162,901 | B2 | 4/2012 | Gonnelli et al. | |
| RE43,399 | E | 5/2012 | Simpson et al. | |
| 8,216,138 | B1 | 7/2012 | McGarraugh | |
| 8,236,368 | B2 | 8/2012 | Jung et al. | |
| 8,249,684 | B2 | 8/2012 | Kamath et al. | |
| 8,257,324 | B2 | 9/2012 | Prausnitz et al. | |
| 8,280,475 | B2 | 10/2012 | Brister et al. | |
| 8,280,476 | B2 | 10/2012 | Jina | |
| 8,284,046 | B2 | 10/2012 | Allen et al. | |
| 8,287,453 | B2 | 10/2012 | Li et al. | |
| 8,308,960 | B2 | 11/2012 | Kalvesten et al. | |
| 8,346,335 | B2 | 1/2013 | Harper et al. | |
| 8,376,945 | B2 | 2/2013 | Hayter et al. | |
| 8,386,004 | B2 | 2/2013 | Kamath et al. | |
| 8,423,114 | B2 | 4/2013 | Simpson et al. | |
| 8,428,678 | B2 | 4/2013 | Kamath et al. | |
| 8,452,369 | B2 * | 5/2013 | Huys | G01N 33/48728 600/372 |
| 8,463,350 | B2 | 6/2013 | Kamath et al. | |
| 8,483,793 | B2 | 7/2013 | Simpson et al. | |
| 8,506,529 | B1 * | 8/2013 | Yang | A61B 5/14514 604/114 |
| 8,548,553 | B2 | 10/2013 | Kamath et al. | |
| 8,565,848 | B2 | 10/2013 | Brister et al. | |
| 8,574,165 | B2 | 11/2013 | Marsh | |
| 8,588,884 | B2 | 11/2013 | Hegde et al. | |
| 8,617,069 | B2 | 12/2013 | Bernstein et al. | |
| RE44,695 | E | 1/2014 | Simpson et al. | |
| 8,626,257 | B2 | 1/2014 | Li et al. | |
| 8,637,351 | B2 | 1/2014 | Kalvesten et al. | |
| 8,660,628 | B2 | 2/2014 | Wang et al. | |
| 8,700,114 | B2 | 4/2014 | Gottlieb et al. | |
| 8,708,966 | B2 | 4/2014 | Allen et al. | |
| 8,798,799 | B2 | 8/2014 | Deo et al. | |
| 8,815,070 | B2 | 8/2014 | Wang et al. | |
| 8,870,763 | B2 | 10/2014 | Yang et al. | |
| 8,882,665 | B2 | 11/2014 | Yang et al. | |
| 8,986,256 | B2 | 3/2015 | Scholten et al. | |
| 9,008,743 | B2 | 4/2015 | Hayter et al. | |
| 9,008,745 | B2 | 4/2015 | Pushpala et al. | |
| 9,055,901 | B2 | 6/2015 | Brister et al. | |
| 9,125,625 | B2 | 9/2015 | Wang et al. | |
| 9,182,368 | B2 | 11/2015 | Pushpala et al. | |
| 9,234,872 | B2 | 1/2016 | Homyk et al. | |
| 9,248,273 | B2 | 2/2016 | Guvanasen et al. | |
| 9,332,934 | B2 | 5/2016 | Hayter et al. | |
| 9,336,423 | B2 | 5/2016 | Goodnow et al. | |
| 9,357,951 | B2 | 6/2016 | Simpson et al. | |
| 9,386,954 | B2 | 7/2016 | Saini et al. | |
| 9,387,000 | B2 | 7/2016 | Corrie et al. | |
| 9,414,778 | B2 | 8/2016 | Mao et al. | |
| 9,420,965 | B2 | 8/2016 | Brauker et al. | |
| 9,498,155 | B2 | 11/2016 | Brauker et al. | |
| 9,532,741 | B2 | 1/2017 | Brauker et al. | |
| 9,551,698 | B2 | 1/2017 | Huys et al. | |
| 9,662,056 | B2 | 5/2017 | Budiman et al. | |

(56) References Cited

U.S. PATENT DOCUMENTS 9,669,156 B2 6/2017 Jennewine
9,737,247 B2 8/2017 Wang et al.
9,743,870 B2 8/2017 Wang et al.
9,743,871 B2 8/2017 Simpson et al.
9,757,061 B2 9/2017 Shults et al.
9,770,211 B2 9/2017 Hayter et al.
9,804,114 B2 10/2017 Rhodes et al.
9,933,387 B1 4/2018 McCANNA et al.
9,958,409 B2 5/2018 Gerber et al.
10,022,076 B2 7/2018 Hoss et al.
10,039,480 B2 8/2018 Brauker et al.
10,046,114 B1 8/2018 Biederman et al.
10,052,055 B2 8/2018 Li et al.
10,092,207 B1 10/2018 Windmiller
10,136,846 B2 11/2018 Wang et al.
10,173,042 B2 1/2019 Pushpala et al.
10,182,748 B2 1/2019 Catt et al.
10,188,333 B2 1/2019 Kamath et al.
10,228,341 B2 3/2019 Katsuki et al.
10,299,712 B2 5/2019 Brister et al.
10,327,678 B2 6/2019 Gottlieb et al.
10,492,708 B1 12/2019 Windmiller
D875,254 S 2/2020 Cooke et al.
10,549,080 B2 2/2020 Pushpala et al.
10,610,103 B2 4/2020 Brister et al.
10,709,332 B2 7/2020 Brister et al.
10,743,800 B2 8/2020 Larvenz et al.
10,780,222 B2 9/2020 Ward et al.
10,820,860 B2 11/2020 Pushpala et al.
10,835,163 B2 11/2020 Haghgooie et al.
10,881,334 B2 1/2021 Facchinetti et al.
10,932,700 B2 3/2021 Simpson et al.
10,983,083 B2 4/2021 Harding et al.
11,020,026 B2 6/2021 Boock et al.
11,035,872 B2 6/2021 Boutelle et al.
11,045,142 B1 6/2021 Windmiller et al.
11,051,724 B2 7/2021 Pace et al.
11,123,532 B2 9/2021 Pushpala et al.
11,179,068 B2 11/2021 Pace et al.
11,197,985 B2 12/2021 Pushpala et al.
11,272,866 B2 3/2022 Pushpala et al.
11,272,885 B2 3/2022 Pushpala et al.
11,291,390 B2 4/2022 Pushpala et al.
11,331,022 B2 5/2022 Halac et al.
11,359,300 B1 6/2022 Beer et al.
11,406,818 B2 8/2022 Windmiller
11,432,747 B2 9/2022 Cho et al.
11,478,194 B2 10/2022 Windmiller et al.
11,596,332 B2 3/2023 Shults et al.
11,654,270 B2 5/2023 Mansfield, III et al.
D988,160 S 6/2023 Morelock
11,672,965 B2 6/2023 Mansfield, III et al.
11,697,007 B2 7/2023 Gu et al.
D996,999 S 8/2023 Morelock
11,819,650 B2 11/2023 Pushpala et al.
D1,012,744 S 1/2024 Morelock
11,857,344 B2 1/2024 Windmiller et al.
11,865,289 B2 1/2024 Pushpala et al.
11,872,055 B2 1/2024 Tangney et al.
D1,013,544 S 2/2024 Morelock
11,896,792 B2 2/2024 Pushpala et al.
11,896,793 B2 2/2024 Pushpala et al.
11,903,738 B2 2/2024 Pushpala et al.
11,904,127 B2 2/2024 Mansfield et al.
11,963,796 B1 4/2024 Windmiller
11,986,614 B2 5/2024 Mansfield et al.
11,992,314 B2 5/2024 Hahn et al.
12,011,294 B2 6/2024 Campbell et al.
D1,033,641 S 7/2024 Morelock
D1,035,004 S 7/2024 Morelock
12,048,558 B2 7/2024 Kendall et al.
D1,038,794 S 8/2024 Morelock
12,070,307 B2 8/2024 Ebejer et al.
12,109,032 B1 10/2024 Windmiller et al.
D1,057,153 S 1/2025 Morelock
D1,068,516 S 4/2025 Morelock
12,279,888 B2 4/2025 Campbell et al.
12,285,271 B2 4/2025 Campbell et al.
12,336,816 B2 6/2025 Campbell et al.
D1,083,640 S 7/2025 Morelock
D1,083,977 S 7/2025 Morelock
12,369,830 B2 7/2025 Windmiller et al.
12,453,516 B2 10/2025 Tangney et al.
12,507,921 B2 12/2025 Alonso-Soski et al.
2002/0004640 A1 1/2002 Conn et al.
2002/0020688 A1 2/2002 Sherman et al.
2002/0055704 A1 5/2002 Scott et al.
2002/0072784 A1 6/2002 Sheppard et al.
2002/0105080 A1 8/2002 Speakman
2002/0120186 A1 8/2002 Keimel
2002/0169393 A1 11/2002 Cunningham et al.
2002/0187556 A1 12/2002 Shartle et al.
2003/0068666 A1 4/2003 Zweig
2003/0078549 A1 4/2003 Stupar et al.
2003/0088166 A1 5/2003 Say et al.
2003/0095582 A1 5/2003 Ackley
2003/0100040 A1 5/2003 Bonnecaze et al.
2003/0104119 A1 6/2003 Wilson et al.
2003/0135158 A1 7/2003 Gonnelli
2003/0135161 A1 7/2003 Fleming et al.
2003/0199788 A1 10/2003 Erickson et al.
2003/0208167 A1 11/2003 Prausnitz et al.
2003/0225360 A1 12/2003 Eppstein et al.
2003/0235817 A1 12/2003 Bartkowiak et al.
2004/0065158 A1 4/2004 Schrepfer et al.
2004/0082875 A1* 4/2004 Donoghue ............... A61B 5/24
600/544
2004/0111017 A1 6/2004 Say et al.
2004/0138543 A1 7/2004 Russell et al.
2004/0146611 A1 7/2004 Arias et al.
2004/0189311 A1 9/2004 Glezer et al.
2004/0220625 A1 11/2004 Silvestri et al.
2005/0013753 A1 1/2005 Eaton et al.
2005/0036020 A1 2/2005 Li et al.
2005/0101841 A9 5/2005 Kaylor et al.
2005/0137536 A1 6/2005 Gonnelli
2005/0209565 A1 9/2005 Yuzhakov et al.
2005/0267440 A1 12/2005 Herman et al.
2005/0272989 A1 12/2005 Shah et al.
2006/0015061 A1 1/2006 Kuo et al.
2006/0016700 A1 1/2006 Brister et al.
2006/0173259 A1 8/2006 Flaherty et al.
2006/0264716 A1 11/2006 Zander
2006/0281121 A1 12/2006 Unger et al.
2007/0020641 A1 1/2007 Heeger et al.
2007/0060815 A1 3/2007 Martin et al.
2007/0078445 A1 4/2007 Malloy
2007/0105404 A1 5/2007 Lee et al.
2007/0151868 A1 7/2007 Staib et al.
2007/0169533 A1 7/2007 Shah et al.
2007/0170054 A2 7/2007 Wilsey
2007/0191700 A1 8/2007 Say et al.
2007/0191733 A1 8/2007 Gianchandani et al.
2007/0213044 A1 9/2007 Steingart et al.
2007/0282246 A1 12/2007 Henley
2008/0009800 A1 1/2008 Nickel
2008/0009801 A1 1/2008 Nickel
2008/0027369 A1 1/2008 Carter et al.
2008/0027426 A1 1/2008 Kelly et al.
2008/0033269 A1 2/2008 Zhang
2008/0097280 A1 4/2008 Martin et al.
2008/0097352 A1 4/2008 Beck et al.
2008/0119707 A1 5/2008 Stafford
2008/0154107 A1 6/2008 Jina
2008/0156661 A1 7/2008 Cooper et al.
2008/0161654 A1 7/2008 Teller et al.
2008/0213461 A1 9/2008 Gill et al.
2008/0221408 A1 9/2008 Hoarau et al.
2008/0234562 A1 9/2008 Jina
2008/0255434 A1 10/2008 Hayter et al.
2008/0275327 A1 11/2008 Faarbaek et al.
2008/0288026 A1 11/2008 Cross et al.
2008/0319298 A1 12/2008 Huys et al.
2009/0043250 A1 2/2009 Gonnelli

(56) References Cited

U.S. PATENT DOCUMENTS

2009/0057148 A1 3/2009 Wieder et al.
2009/0062752 A1 3/2009 Gonnelli
2009/0066348 A1 3/2009 Shin et al.
2009/0069650 A1 3/2009 Jennewine
2009/0069651 A1 3/2009 Zimmermann et al.
2009/0069697 A1 3/2009 Frazier et al.
2009/0084678 A1 4/2009 Joshi et al.
2009/0088652 A1 4/2009 Tremblay
2009/0090623 A1 4/2009 Chuang et al.
2009/0099427 A1 4/2009 Jina et al.
2009/0101498 A1 4/2009 Papadimitrakopoulo et al.
2009/0118672 A1 5/2009 Gonnelli et al.
2009/0131778 A1 5/2009 Jina et al.
2009/0143761 A1 6/2009 Cantor et al.
2009/0152598 A1 6/2009 Baek et al.
2009/0157330 A1 6/2009 Rinne et al.
2009/0191616 A1 7/2009 Lu et al.
2009/0198118 A1 8/2009 Hayter et al.
2009/0218239 A1 9/2009 Gooding et al.
2009/0234202 A1 9/2009 Goix et al.
2009/0259118 A1 10/2009 Feldman et al.
2009/0294306 A1 12/2009 Feldman et al.
2009/0301994 A1 12/2009 Bhandari et al.
2010/0006451 A1 1/2010 Gordon et al.
2010/0021637 A1 1/2010 Revol Cavalier et al.
2010/0022416 A1 1/2010 Flemming et al.
2010/0025238 A1 2/2010 Gottlieb et al.
2010/0030045 A1 2/2010 Gottlieb et al.
2010/0049021 A1 2/2010 Jina et al.
2010/0052892 A1 3/2010 Allen et al.
2010/0052897 A1 3/2010 Allen et al.
2010/0052898 A1 3/2010 Allen et al.
2010/0052915 A1 3/2010 Allen et al.
2010/0056873 A1 3/2010 Allen et al.
2010/0108509 A1 5/2010 Curry et al.
2010/0137779 A1 6/2010 Seitz
2010/0160756 A1 6/2010 Petisce et al.
2010/0200538 A1 8/2010 Petisce et al.
2010/0213079 A1 8/2010 Willis
2010/0268043 A1 10/2010 Yodfat et al.
2010/0279377 A1 11/2010 Shah et al.
2010/0286803 A1 11/2010 Tillotson et al.
2011/0027127 A1 2/2011 Simpson et al.
2011/0042241 A1 2/2011 Kotsis et al.
2011/0077490 A1 3/2011 Simpson et al.
2011/0105871 A1 5/2011 Zimmermann et al.
2011/0140703 A1 6/2011 Chiao et al.
2011/0196216 A1 8/2011 Quarder et al.
2011/0210017 A1 9/2011 Lai et al.
2011/0224515 A1 9/2011 Mir et al.
2011/0230736 A1 9/2011 Tepper et al.
2011/0237925 A1 9/2011 Yue et al.
2011/0247934 A1 10/2011 Wang et al.
2011/0275918 A1 11/2011 Yamashita et al.
2011/0306853 A1 12/2011 Black et al.
2011/0319787 A1 12/2011 Lamoise et al.
2012/0018302 A1 1/2012 Shiraki et al.
2012/0037515 A1 2/2012 Solanki
2012/0067734 A1 3/2012 Wang et al.
2012/0078071 A1 3/2012 Bohm et al.
2012/0123232 A1 5/2012 Najarian et al.
2012/0172692 A1 7/2012 Tamada et al.
2012/0209244 A1 8/2012 Gray
2012/0277629 A1 11/2012 Bernstein et al.
2012/0323097 A9 12/2012 Chowdhury
2013/0053660 A1 2/2013 Shieh
2013/0065257 A1 3/2013 Wang et al.
2013/0135158 A1 5/2013 Faraone et al.
2013/0144131 A1 6/2013 Wang et al.
2013/0158376 A1 6/2013 Hayter et al.
2013/0197338 A1 8/2013 Yu et al.
2013/0225956 A1 8/2013 Huang et al.
2013/0281808 A1 10/2013 Shieh
2013/0324820 A1 12/2013 Petillo et al.
2013/0338632 A1 12/2013 Kaplan et al.
2013/0338746 A1 12/2013 Guvanasen et al.
2013/0345597 A1 12/2013 Hagino et al.
2014/0135679 A1 5/2014 Mann et al.
2014/0259652 A1 9/2014 Pushpala et al.
2014/0275897 A1 9/2014 Pushpala et al.
2014/0275899 A1 9/2014 Gottlieb et al.
2014/0275907 A1 9/2014 Feldman et al.
2014/0303471 A1 10/2014 Rajaraman et al.
2014/0336487 A1 11/2014 Wang et al.
2014/0378804 A1 12/2014 Kalvesten et al.
2015/0073238 A1 3/2015 Matsumoto et al.
2015/0126834 A1 5/2015 Wang et al.
2015/0186609 A1 7/2015 Utter II
2015/0208970 A1 7/2015 Huang
2015/0208985 A1 7/2015 Huang
2015/0243851 A1 8/2015 Lee et al.
2015/0250421 A1 9/2015 Arumugam et al.
2015/0276758 A1 10/2015 Addisu
2015/0313527 A1 11/2015 Renlund
2015/0351670 A1 12/2015 Vanslyke et al.
2016/0022187 A1 1/2016 Pushpala et al.
2016/0029937 A1 2/2016 Sia et al.
2016/0029966 A1 2/2016 Salas-Boni et al.
2016/0058342 A1* 3/2016 Maiz-Aguinaga .......................... A61B 5/14514 600/345
2016/0095541 A1 4/2016 Wang et al.
2016/0095547 A1 4/2016 Wang et al.
2016/0139069 A1 5/2016 Wang
2016/0157764 A1 6/2016 Di Palma et al.
2016/0158514 A1 6/2016 Stoeber et al.
2016/0162662 A1 6/2016 Monirabbasi et al.
2016/0166184 A1 6/2016 Teng et al.
2016/0166186 A1 6/2016 Ferguson et al.
2016/0213908 A1 7/2016 McALLISTER et al.
2016/0258945 A1 9/2016 Malima et al.
2016/0270704 A1 9/2016 DeTURK
2016/0296149 A1* 10/2016 Polsky ............... A61B 5/14546
2016/0302687 A1* 10/2016 Lee .......................... A61B 5/05
2016/0324442 A1 11/2016 Zdeblick
2016/0370377 A1 12/2016 Ahmad
2017/0003766 A1 1/2017 Budiman
2017/0007813 A1 1/2017 Negi et al.
2017/0035331 A1 2/2017 Paranjape et al.
2017/0055835 A1 3/2017 Scherer et al.
2017/0086713 A1 3/2017 Pushpala et al.
2017/0108459 A1 4/2017 Katsuki et al.
2017/0127989 A1 5/2017 Feldman et al.
2017/0128009 A1 5/2017 Pushpala et al.
2017/0164881 A1 6/2017 Fujita et al.
2017/0172475 A1 6/2017 Pushpala et al.
2017/0238851 A1 8/2017 Duhamel et al.
2017/0251958 A1 9/2017 Pushpala et al.
2017/0251959 A1 9/2017 Feldman et al.
2017/0251960 A1 9/2017 Crouther et al.
2017/0311852 A1 11/2017 Morgan
2017/0347925 A1 12/2017 Wang et al.
2017/0347926 A1 12/2017 Farooqui
2018/0014787 A1 1/2018 Ganton et al.
2018/0116572 A1 5/2018 Simpson et al.
2018/0140235 A1 5/2018 Pushpala et al.
2018/0256086 A1 9/2018 Polsky et al.
2018/0279929 A1* 10/2018 Huang ............. A61B 5/150022
2018/0317820 A1 11/2018 Pace et al.
2018/0338712 A1* 11/2018 Cass .................. A61B 5/14514
2018/0338713 A1 11/2018 Polsky et al.
2018/0340203 A1 11/2018 Holmes et al.
2019/0001108 A1 1/2019 Ono
2019/0008425 A1 1/2019 Srinivasan et al.
2019/0008433 A1 1/2019 Peyser et al.
2019/0022365 A1 1/2019 Chowdhury et al.
2019/0029577 A1 1/2019 Koelker et al.
2019/0076075 A1 3/2019 Miller et al.
2019/0090811 A1 3/2019 Reitz et al.
2019/0091455 A1 3/2019 Reitz et al.
2019/0094169 A1 3/2019 Shah et al.
2019/0101551 A1 4/2019 Plaxco et al.
2019/0110724 A1 4/2019 Kamath et al.
2019/0125223 A1 5/2019 Wang et al.

(56) References Cited

U.S. PATENT DOCUMENTS

| | | | |
|---|---|---|---|
| 2019/0167167 | A1 | 6/2019 | Mitchell et al. |
| 2019/0170739 | A1 | 6/2019 | Garner et al. |
| 2019/0201675 | A1 | 7/2019 | Miller et al. |
| 2019/0209095 | A1 | 7/2019 | Kamath et al. |
| 2019/0223795 | A1 | 7/2019 | Patolsky et al. |
| 2019/0224712 | A1 | 7/2019 | Petisce et al. |
| 2019/0231263 | A1 | 8/2019 | Ribet et al. |
| 2019/0241926 | A1 | 8/2019 | Mckinlay et al. |
| 2019/0261907 | A1 | 8/2019 | Brister et al. |
| 2019/0274599 | A1 | 9/2019 | Polsky et al. |
| 2019/0274600 | A1 | 9/2019 | Pesantez et al. |
| 2019/0298210 | A1 | 10/2019 | Bennet et al. |
| 2019/0307379 | A1 | 10/2019 | Boock et al. |
| 2019/0309433 | A1 | 10/2019 | Sattayasamitsathit et al. |
| 2019/0310219 | A1 | 10/2019 | Boock |
| 2019/0328938 | A1 | 10/2019 | Son |
| 2019/0357827 | A1 | 11/2019 | Li et al. |
| 2019/0358441 | A1 | 11/2019 | Zvezdin et al. |
| 2020/0000387 | A1 | 1/2020 | Gerhardt et al. |
| 2020/0029876 | A1 | 1/2020 | Brister et al. |
| 2020/0037938 | A1 | 2/2020 | Rong et al. |
| 2020/0046272 | A1 | 2/2020 | Brister et al. |
| 2020/0101286 | A1 | 4/2020 | Windmiller et al. |
| 2020/0121902 | A1 | 4/2020 | Pushpala et al. |
| 2020/0138343 | A1 | 5/2020 | Gerasopoulos et al. |
| 2020/0178853 | A1 | 6/2020 | Pushpala et al. |
| 2020/0187778 | A1 | 6/2020 | Brister et al. |
| 2020/0214566 | A1 | 7/2020 | Allen et al. |
| 2020/0254240 | A1 | 8/2020 | Windmiller et al. |
| 2020/0297997 | A1 | 9/2020 | Windmiller et al. |
| 2020/0305771 | A1 | 10/2020 | Feldman et al. |
| 2020/0330007 | A1 | 10/2020 | Garai et al. |
| 2020/0359949 | A1 | 11/2020 | Brauker et al. |
| 2020/0390395 | A1 | 12/2020 | Pushpala et al. |
| 2020/0405234 | A1 | 12/2020 | Pushpala et al. |
| 2021/0045663 | A1 | 2/2021 | Simpson et al. |
| 2021/0045665 | A1 | 2/2021 | Simpson et al. |
| 2021/0045666 | A1 | 2/2021 | Simpson et al. |
| 2021/0060322 | A1 | 3/2021 | Burton |
| 2021/0100452 | A1 | 4/2021 | Brister et al. |
| 2021/0100504 | A1 | 4/2021 | Pushpala et al. |
| 2021/0100505 | A1 | 4/2021 | Pushpala et al. |
| 2021/0183508 | A1 | 6/2021 | Parker et al. |
| 2021/0187286 | A1 | 6/2021 | Windmiller et al. |
| 2021/0190719 | A1 | 6/2021 | Latour et al. |
| 2021/0236057 | A1 | 8/2021 | Pushpala et al. |
| 2021/0321942 | A1 | 10/2021 | Pushpala et al. |
| 2021/0345916 | A1 | 11/2021 | Boock et al. |
| 2021/0353229 | A1 | 11/2021 | Pierart et al. |
| 2021/0379370 | A1 | 12/2021 | Windmiller et al. |
| 2021/0386338 | A1 | 12/2021 | Zhang et al. |
| 2021/0393201 | A1 | 12/2021 | Morelock et al. |
| 2022/0031244 | A1 | 2/2022 | Windmiller et al. |
| 2022/0047190 | A1 | 2/2022 | Taylor et al. |
| 2022/0054813 | A1 | 2/2022 | Pushpala et al. |
| 2022/0054814 | A1 | 2/2022 | Pushpala et al. |
| 2022/0104773 | A1 | 4/2022 | Lee et al. |
| 2022/0151516 | A1 | 5/2022 | Wang et al. |
| 2022/0151518 | A1 | 5/2022 | Pushpala et al. |
| 2022/0151519 | A1 | 5/2022 | Pushpala et al. |
| 2022/0151558 | A1 | 5/2022 | Pushpala et al. |
| 2022/0175278 | A1 | 6/2022 | Campbell et al. |
| 2022/0175279 | A1 | 6/2022 | Pushpala et al. |
| 2022/0175282 | A1 | 6/2022 | Hoss et al. |
| 2022/0214300 | A1 | 7/2022 | Wang et al. |
| 2022/0225901 | A1 | 7/2022 | Chapman et al. |
| 2022/0233107 | A1 | 7/2022 | Pushpala et al. |
| 2022/0241569 | A1 | 8/2022 | Quan et al. |
| 2022/0249189 | A1 | 8/2022 | Choi et al. |
| 2022/0257181 | A1 | 8/2022 | Wang et al. |
| 2022/0298291 | A1 | 9/2022 | Shin et al. |
| 2022/0322975 | A1 | 10/2022 | Baker et al. |
| 2022/0322977 | A1 | 10/2022 | Simpson et al. |
| 2022/0361776 | A1 | 11/2022 | Wang et al. |
| 2022/0370011 | A1 | 11/2022 | Windmiller et al. |
| 2023/0003725 | A1 | 1/2023 | Wang et al. |
| 2023/0012662 | A1 | 1/2023 | Tehrani et al. |
| 2023/0074798 | A1 | 3/2023 | Tangney et al. |
| 2023/0094419 | A1 | 3/2023 | Mansfield, III et al. |
| 2023/0099617 | A1 | 3/2023 | Mansfield, III et al. |
| 2023/0137258 | A1 | 5/2023 | Windmiller |
| 2023/0190147 | A1 | 6/2023 | Campbell et al. |
| 2023/0256220 | A1 | 8/2023 | Mansfield, III et al. |
| 2023/0301552 | A1 | 9/2023 | Mallires et al. |
| 2023/0310823 | A1 | 10/2023 | Mansfield, III et al. |
| 2023/0414102 | A1 | 12/2023 | Allen et al. |
| 2024/0008777 | A1 | 1/2024 | Fuchs et al. |
| 2024/0081740 | A1 | 3/2024 | Windmiller et al. |
| 2024/0164719 | A1 | 5/2024 | Campbell et al. |
| 2024/0252115 | A1 | 8/2024 | Tangney et al. |
| 2024/0315614 | A1 | 9/2024 | Campbell et al. |
| 2024/0337620 | A1 | 10/2024 | Iketani et al. |
| 2024/0341636 | A1 | 10/2024 | Yang et al. |
| 2024/0366125 | A1 | 11/2024 | Alonso-Soski et al. |
| 2024/0366149 | A1 | 11/2024 | Kendall et al. |
| 2024/0423526 | A1 | 12/2024 | Windmiller et al. |
| 2025/0000395 | A1 | 1/2025 | Brister et al. |
| 2025/0009301 | A1 | 1/2025 | Gross et al. |
| 2025/0049397 | A1 | 2/2025 | Campbell et al. |
| 2025/0213859 | A1 | 7/2025 | Windmiller et al. |
| 2025/0281080 | A1 | 9/2025 | Campbell et al. |
| 2025/0311950 | A1 | 10/2025 | Poudineh et al. |
| 2025/0331758 | A1 | 10/2025 | Windmiller et al. |
| 2026/0013755 | A1 | 1/2026 | Harris et al. |
| 2026/0026749 | A1 | 1/2026 | Windmiller et al. |

FOREIGN PATENT DOCUMENTS

| | | | |
|---|---|---|---|
| AU | 2012326664 | A1 | 4/2014 |
| CN | 101068591 | A | 11/2007 |
| CN | 108404286 | A | 8/2018 |
| CN | 108845012 | A | 11/2018 |
| CN | 211357412 | U | 8/2020 |
| CN | 112617822 | A | 4/2021 |
| CN | 113352654 | A | 9/2021 |
| CN | 113648529 | A | 11/2021 |
| CN | 113717955 | A | 11/2021 |
| CN | 114010934 | A | 2/2022 |
| CN | 114129503 | A | 3/2022 |
| DE | 102008048984 | A1 | 4/2010 |
| DE | 102015209669 | A1 | 12/2016 |
| EP | 1377338 | A2 | 1/2004 |
| EP | 1006868 | B1 | 6/2004 |
| EP | 1372602 | B1 | 4/2007 |
| EP | 1377338 | B1 | 8/2008 |
| EP | 1792565 | B1 | 10/2008 |
| EP | 1187653 | B1 | 3/2010 |
| EP | 2359885 | A1 | 8/2011 |
| EP | 2898821 | B1 | 12/2017 |
| EP | 3285851 | A1 | 2/2018 |
| EP | 3364183 | A1 | 8/2018 |
| EP | 3381370 | A1 | 10/2018 |
| EP | 3829418 | B1 | 11/2024 |
| EP | 3829437 | B1 | 11/2024 |
| EP | 4009865 | B1 | 11/2024 |
| EP | 4482372 | A1 | 1/2025 |
| FR | 3099696 | A1 | 2/2021 |
| JP | H0222552 | A | 1/1990 |
| JP | H0231741 | A | 2/1990 |
| JP | H05215712 | A | 8/1993 |
| JP | H067324 | A | 1/1994 |
| JP | H07275227 | A | 10/1995 |
| JP | 2002513602 | A | 5/2002 |
| JP | 2003038464 | A | 2/2003 |
| JP | 2003038465 | A | 2/2003 |
| JP | 2003111742 | A | 4/2003 |
| JP | 2004180773 | A | 7/2004 |
| JP | 2005087613 | A | 4/2005 |
| JP | 2005525141 | A | 8/2005 |
| JP | 2005322591 | A | 11/2005 |
| JP | 2006510467 | A | 3/2006 |
| JP | 2008506468 | A | 3/2008 |
| JP | 2008512162 | A | 4/2008 |
| JP | 2008540013 | A | 11/2008 |

(56) References Cited

FOREIGN PATENT DOCUMENTS

| | | | |
|---|---|---|---|
| JP | 2008544763 | A | 12/2008 |
| JP | 2009544409 | A | 12/2009 |
| JP | 2010523167 | A | 7/2010 |
| JP | 5053330 | B2 | 10/2012 |
| JP | 2013506847 | A | 2/2013 |
| JP | 2013521942 | A | 6/2013 |
| JP | 2014533523 | A | 12/2014 |
| JP | 2017512118 | A | 5/2017 |
| JP | 2017108763 | A | 6/2017 |
| JP | 2018019826 | A | 2/2018 |
| JP | 2019506910 | A | 3/2019 |
| JP | 2019107040 | A | 7/2019 |
| JP | 2019526332 | A | 9/2019 |
| JP | 2019205852 | A | 12/2019 |
| JP | 2020527063 | A | 9/2020 |
| JP | 2020170011 | A | 10/2020 |
| JP | 2022501100 | A | 1/2022 |
| JP | 2022508575 | A | 1/2022 |
| KR | 100793615 | B1 | 1/2008 |
| KR | 20140078644 | A | 6/2014 |
| KR | 101621945 | B1 | 5/2016 |
| KR | 20160108111 | A | 9/2016 |
| KR | 20160123951 | A | 10/2016 |
| KR | 20170041375 | A | 4/2017 |
| KR | 20180127729 | A | 11/2018 |
| KR | 20190092383 | A | 8/2019 |
| WO | WO-0074763 | A2 | 12/2000 |
| WO | WO-2006017358 | A1 | 2/2006 |
| WO | WO-2006060106 | A1 | 6/2006 |
| WO | WO-2006062668 | A2 | 6/2006 |
| WO | WO-2006093422 | A1 | 9/2006 |
| WO | WO-2006116242 | A2 | 11/2006 |
| WO | WO-2007040938 | A1 | 4/2007 |
| WO | WO-2008013881 | A2 | 1/2008 |
| WO | WO-2008094249 | A1 | 8/2008 |
| WO | WO-2009034313 | A2 | 3/2009 |
| WO | WO-2009064164 | A2 | 5/2009 |
| WO | WO-2009124095 | A1 | 10/2009 |
| WO | WO-2010014959 | A2 | 2/2010 |
| WO | WO-2010022252 | A2 | 2/2010 |
| WO | WO-2010045247 | A1 | 4/2010 |
| WO | WO-2010059276 | A1 | 5/2010 |
| WO | WO-2010120364 | A2 | 10/2010 |
| WO | WO-2011041715 | A2 | 4/2011 |
| WO | WO-2011056095 | A1 | 5/2011 |
| WO | WO-2011115949 | A1 | 9/2011 |
| WO | WO-2012020332 | A2 | 2/2012 |
| WO | WO-2012142625 | A2 | 10/2012 |
| WO | WO-2013058879 | A2 | 4/2013 |
| WO | WO-2014120114 | A1 | 8/2014 |
| WO | WO-2015073459 | A1 | 5/2015 |
| WO | WO-2016009228 | A1 | 1/2016 |
| WO | WO-2016167626 | A1 | 10/2016 |
| WO | WO-2016189301 | A1 | 12/2016 |
| WO | WO-2017129980 | A1 | 8/2017 |
| WO | WO-2017189707 | A1 | 11/2017 |
| WO | WO-2018017196 | A1 | 1/2018 |
| WO | WO-2018037407 | A1 | 3/2018 |
| WO | WO-2018071265 | A1 | 4/2018 |
| WO | WO-2018164886 | A1 | 9/2018 |
| WO | WO-2018170363 | A1 | 9/2018 |
| WO | WO-2019046333 | A1 | 3/2019 |
| WO | WO-2019156934 | A1 | 8/2019 |
| WO | WO-2019222615 | A1 | 11/2019 |
| WO | WO-2019239258 | A1 | 12/2019 |
| WO | WO-2020023804 | A1 | 1/2020 |
| WO | WO-2020069565 | A1 | 4/2020 |
| WO | WO-2020069567 | A1 | 4/2020 |
| WO | WO-2020069570 | A1 | 4/2020 |
| WO | WO-2020117918 | A1 | 6/2020 |
| WO | WO-2020186118 | A1 | 9/2020 |
| WO | WO-2021007344 | A1 | 1/2021 |
| WO | WO-2021015389 | A1 | 1/2021 |
| WO | WO-2021025260 | A1 | 2/2021 |
| WO | WO-2021062475 | A1 | 4/2021 |
| WO | WO-2021081456 | A1 | 4/2021 |
| WO | WO-2021086690 | A1 | 5/2021 |
| WO | WO-2021118124 | A1 | 6/2021 |
| WO | WO-2021118431 | A1 | 6/2021 |
| WO | WO-2021119546 | A1 | 6/2021 |
| WO | WO-2021216186 | A9 | 12/2021 |
| WO | WO-2021216186 | A3 | 1/2022 |
| WO | WO-2022026764 | A1 | 2/2022 |
| WO | WO-2022066985 | A1 | 3/2022 |
| WO | WO-2022066992 | A1 | 3/2022 |
| WO | WO-2022090741 | A1 | 5/2022 |
| WO | WO-2022136785 | A1 | 6/2022 |
| WO | WO-2022170283 | A1 | 8/2022 |
| WO | WO-2022240700 | A1 | 11/2022 |
| WO | WO-2023055755 | A1 | 4/2023 |
| WO | WO-2023064877 | A1 | 4/2023 |
| WO | WO-2023133468 | A1 | 7/2023 |
| WO | WO-2023229662 | A2 | 11/2023 |
| WO | WO-2024000015 | A1 | 1/2024 |
| WO | WO-2024010827 | A1 | 1/2024 |
| WO | WO-2024163950 | A2 | 8/2024 |
| WO | WO-2024238798 | A1 | 11/2024 |
| WO | WO-2025144429 | A2 | 7/2025 |
| WO | WO-2025231565 | A1 | 11/2025 |

OTHER PUBLICATIONS

Allen et al., "Continuous glucose monitoring counseling improves physical activity behaviors of individuals with type 2 diabetes: A randomized clinical trial" Diabetes Res Clin Pract. Jun. 2008 80(3): 371-379. doi:10.1016/j.diabres.2008.01.006.

American Diabetes Association, "Diabetes and Emotional Health: A Practical Guide for Health Professionals Supporting Adults with Type 1 and Type 2 Diabetes" U.S. Edition (2021), 214 pages.

American Diabetes Association® Press Release (2020). "American Diabetes Association® Applauds policymakers' Focus on Addressing High Costs of Insulin for Seven Million Americans," 4 pages.

American Diabetes Association Professional Practice Committee, "6. Glycemic Goals and Hypoglycemia: Standards of Care in Diabetes-2024" Diabetes Care Jan. 1, 2024; 47(Suppl 1):S111-S125.

American Diabetes Association Professional Practice Committee, "7. Diabetes Technology: Standards of Medical Care in Diabetes-2022" Diabetes Care Jan 1, 2022; 45(Suppl 1):S97-S112.

Bantle, J.P et al. (1997). "Glucose measurement in patients with diabetes mellitus with dermal interstitial fluid," J. Lab. Clin. Med. 130:436-441.

Barrett et al., "Risk for Newly Diagnosed Diabetes 30 Days After SARS-COV-2 Infection Among Persons Aged 18 Years—United States, March 1, 2020-Jun. 28, 2021" MMWR Morb Mortal Wkly Rep. Jan. 14, 2022; 71(2):59-65. doi: 10.15585/mmwr.mm7102e2.

Beckles, G.L. et al. (2016). "Disparities in the prevalence of diagnosed diabetes—United States, 1999-2002 and 2011-2014," MMWR 65:1265-1269.

Brown, "Design of Electronics for Wearable Electrochemical Sensors" University of California, San Diego, Master's Thesis (2019) 48 pages.

Cao, J. et al. (2017). "Validation of capillary blood analysis and capillary testing mode on the epoc Point of Care system," Pract. Lab. Med. 9:24-27.

Castle, J.R. et al. (2012). "The accuracy benefit of multiple amperometric glucose sensors in people with type 1 diabetes," Diabetes Care 35:706-710.

Centers for Disease Control, "National Diabetes Statistics Report 2020 Estimates of Diabetes and Its Burden in the United States" (2020) 32 pages.

Centers for Disease Control, "National Diabetes Statistics Report" May 2024, 16 pages.

Chang, H. et al. (2017). "A swellable microneedle patch to rapidly extract skin interstitial fluid for timely metabolic analysis," Adv. Mater. 29:1702243. 8 pages.

Chen et al., "Electrochemically Mediated Electrodeposition/Electropolymerization To Yield a Glucose Microbiosensor with Improved Characteristics" Anal. Chem. (2002) 74:368-372.

(56) References Cited

OTHER PUBLICATIONS

Diabetes Care (2021). "7. Diabetes Technology: Standards of Medical Care in Diabetes—2021," Diabetes Care 44(Supplement 1):S85-S99.
Diabetes Control and Complications Trial Research Group, "The effect of intensive treatment of diabetes on the development and progression of long-term complications in insulin-dependent diabetes mellitus" N Engl J Med Sep. 30, 1993; 329(14):977-986.
Donnelly, R.F. et al. (2007). "Microstructured Devices for Transdermal Drug Delivery and Minimally-Invasive Patient Monitoring," Recent Patents on Drug Delivery & Formulation 1:195-200.
Dunkin et al., "Scarring occurs at a critical depth of skin injury: precise measurement in a graduated dermal scratch in human volunteers" Plast Reconstr Surg. May 2007; 119(6):1722-1732. doi: 10.1097/01.prs.0000258829.07399.f0.
Ehrhardt et al., "Behavior Modification in Prediabetes and Diabetes: Potential Use of Real-Time Continuous Glucose Monitoring " Journal of Diabetes Science and Technology (2019) Mar. 2019;13(2):271-275.
Ehrhardt et al., "Continuous Glucose Monitoring As a Behavior Modification Tool" Clin Diabetes. Apr. 2020; 38(2):126-131. doi: 10.2337/cd19-0037.
Ehrhardt et al., "The Effect of Real-Time Continuous Glucose Monitoring on Glycemic Control in Patients with Type 2 Diabetes Mellitus" Journal of Diabetes Science and Technology May 2021; 5(3):668-675.
Elsayed et al., "2. Classification and Diagnosis of Diabetes: Standards of Care in Diabetes-2023" Diabetes Care Jan 1, 2023; 46(Suppl 1):S19-S40.
Extended European Search Report for European Application No. 23218205.5 dated Jun. 11, 2024, 7 pages.
Extended European Search Report for European Application No. EP20898007.8 dated Nov. 29, 2023, 9 pages.
Extended European Search Report for European Application No. EP21837561.6 dated Jun. 21, 2024, 7 pages.
Extended European Search Report mailed on Mar. 30, 2023, for European Application No. EP20881425.1, 8 pages.
Extended European Search Report mailed on May 8, 2015, for EP Application No. 12842020.5, filed on Aug. 31, 2012, 7 pages.
Extended European Search Report mailed on Oct. 27, 2022, for EP Application No. 21850331.6, filed on Jul. 29, 2021, 8 pages.
Fang, M et al. (2021). "Trends in Diabetes Treatment and Control in U.S. Adults, 1999-2018," N. Engl. J. Med. 384:2219-2228.
Final Office Action mailed on Aug. 15, 2022, for U.S. Appl. No. 16/051,398, filed Jul. 31, 2018, 15 pages.
Final Office Action mailed on Aug. 19, 2016, for U.S. Appl. No. 14/965,755, filed Dec. 10, 2015, 17 pages.
Final Office Action mailed on Aug. 29, 2023, for U.S. Appl. No. 18/086,543, filed Dec. 21, 2022, 17 pages.
Final Office Action mailed on Dec. 7, 2020, for U.S. Appl. No. 15/961,793, filed Apr. 24, 2018, 13 pages.
Final Office Action mailed on Feb. 1, 2024, for U.S. Appl. No. 17/073,331, filed Oct. 17, 2020, 12 pages.
Final Office Action mailed on Feb. 8, 2024, for U.S. Appl. No. 16/051,398, filed Jul. 31, 2018, 15 pages.
Final Office Action mailed on Jun. 9, 2021, for U.S. Appl. No. 16/169,939, filed Oct. 24, 2018, 24 pages.
Final Office Action mailed on Mar. 15, 2024, for U.S. Appl. No. 17/367,274, filed Jul. 2, 2021, 33 pages.
Final Office Action mailed on May 18, 2018, for U.S. Appl. No. 15/687,145, filed Aug. 25, 2017, 23 pages.
Final Office Action mailed on May 21, 2021, for U.S. Appl. No. 16/051,398, filed Jul. 31, 2018, 11 pages.
Final Office Action mailed on May 9, 2022, for U.S. Appl. No. 17/389,153, filed Jul. 29, 2021, 17 pages.
Final Office Action mailed on Nov. 27, 2023, for U.S. Appl. No. 17/389,156, filed Jul. 29, 2021, 29 pages.
Final Office Action mailed on Nov. 28, 2016, for U.S. Appl. No. 14/342,536, filed Jul. 30, 2014, 34 pages.
Final Office Action mailed on Oct. 27, 2022, for U.S. Appl. No. 15/913,709, filed Mar. 6, 2018, 21 pages.
Final Office Action mailed on Sep. 23, 2021, for U.S. Appl. No. 15/913,709, filed Mar. 6, 2018, 17 pages.
Fonda et al., "The Cost-Effectiveness of Real-Time Continuous Glucose Monitoring (RT-CGM) in Type 2 Diabetes" Journal of Diabetes Science and Technology (2016) 10(4):898-904.
French, D.P. et al. (2008). "Original Article: Psychological Care Self-monitoring of blood glucose changed non-insulin-treated Type 2 diabetes patients' beliefs about diabetes and self-monitoring in a randomized trial," Diav. Med. 25:1218-1228.
Gittard, S.D. et al. (2009). "Fabrication of Polymer Microneedles Using a Two-Photon Polymerization and Micromolding Process," J. Diabetes Sci. Technol. 3:304-311.
Grady, M. et al. (2017). "Examining the Impact of a Novel Blood Glucose Monitor with Color Range Indicator on Decision-Making in Patients With Type 1 and Type 2 Diabetes and its Association With Patient Numeracy Level," JMIR Diabetes 2:e24. 11 pages.
Grady, M. et al. (2018). "Use of Blood Glucose Meters Featuring Color Range Indicators Improves Glycemic Control in Patients with Diabetes in Comparison to Blood Glucose Meters Without Color (ACCENTS Study)," J. Diab. Sci. Tech. 12:1211-1219.
Groenendaal, W. et al. (2008). "Modeling Glucose and Water Dynamics in Human Skin," Diab. Tech. Therap. 10:283-293.
Han et al., "The End of the Road for the YSI 2300 Analyzer: Where Do We Go Now?" Journal of Diabetes Science and Technology (2020) 14(3):595-600.
Han et al., "The YSI 2300 Analyzer Replacement Meeting Report" Journal of Diabetes Science and Technology (2020) 14(3):679-686.
International Search Report and Written Opinion for Application No. PCT/US2022/028196, mailed on Aug. 29, 2022, 8 pages.
International Search Report and Written Opinion for PCT Application No. PCT/US2020/064700, mail date Mar. 9, 2021, 11 pages.
International Search Report and Written Opinion mailed on Feb. 6, 2024, for International Application No. PCT/US2022/078819, filed on Oct. 27, 2022, 13 pages.
International Search Report mailed on Dec. 30, 2021, for PCT Application No. PCT/US2021/043786, filed on Jul. 29, 2021, 7 pages.
International Search Report mailed on Feb. 4, 2021, for PCT Application No. PCT/US2020/056517, filed on Oct. 20, 2020,2 pages.
International Search Report mailed on Jun. 27, 2013, for PCT Application No. PCT/US2012/053544, filed on Aug. 31, 2012, 4 pages.
International Search Report mailed on Sep. 10, 2020, for PCT Application No. PCT/US2020/037379, filed on Jun. 12, 2020, 2 pages.
International Search Report mailed on Sep. 30, 2021, for PCT Application No. PCT/US2021/040385, filed on Jul. 2, 2021, 2 pages.
Invitation to pay additional fees for International Application No. PCT/US2024/014324, dated Jul. 30, 2024, 16 pages.
Jeon, G. et al. (2011). "Electrically Actuatable Smart Nanoporous Membrane for Pulsatile Drug Release," Nano Lett. 11:1284-1288.
Jina, A. et al. (2014). "Design, development, and evaluation of a novel microneedle array-based continuous glucose monitor," J. Diabetes Sci. Technol. 8:483-487.
Juvenile Diabetes Research Foundation Continuous Glucose Monitoring Study Group (2008). "Continuous Glucose Monitoring and Intensive Treatment of Type 1 Diabetes," N. Engl. Med. 359:1464-1476.
Karter, A.J. et al. (2021). "Association of Real-time Continuous Glucose Monitoring With Glycemic Control and Acute Metabolic Events Among Patients With Insulin-Treated Diabetes," JAMA 325:2273-2284.
Lhernould, M.S. et al. (2015). "Review of Patents for Microneedle Application Devices Allowing Fluid Injections Through the Skin," Recent Patents on Drug Delivery & Formulation 9:146-157.
Malitesta et al. (1990). "Glucose fast-response amperometric sensor based on glucose oxidase immobilized in an electropolymerized poly(o-phenylenediamine) film," Anal. Chem. 62:2735-2740.

(56) References Cited

OTHER PUBLICATIONS

Martens, T. et al. (2021). "Effect of Continuous Glucose Monitoring on Glycemic Control in Patients with Type 2 Diabetes Treated with Basal Insulin A Randomized Clinical Trial," JAMA 325:2262-2272.
McClatchey, P.M et al. (2019). "Fibrotic Encapsulation Is the Dominant Source of Continuous Glucose Monitor Delays," Diabetes 68:1892-1901.
Mendes-Soares et al., "Assessment of a Personalized Approach to Predicting Postprandial Glycemic Responses to Food Among Individuals Without Diabetes" JAMA Network Open Feb. 1, 2019; 2(2):e188102. 13 pages.
Miller et al., "Hypoglycemia in patients with type 2 diabetes mellitus" Arch Intern Med Jul. 9, 2001; 161(13):1653-1659.
Miller, P.R. et al. (2011). "Integrated carbon fiber electrodes within hollow polymer microneedles for transdermal electrochemical sensing," BioMicrofluidics 5(1):013415. 14 pages.
Mohan, A.M. (2017). "Continuous minimally-invasive alcohol monitoring using microneedle sensor arrays," Biosensors and Bioelectronics 91:574-579.
Neerken, S. et al. (2004). "Characterization of age-related effects in human skin: A comparative study that applies confocal laser scanning microscopy and optical coherence tomography," J. Biomed. Optics 9:274-281.
Newton et al., "Diabetic ketoacidosis in type 1 and type 2 diabetes mellitus: clinical and biochemical differences" Arch Intern Med Sep. 27, 2004; 164(17):1925-1931.
Non-Final Office Action for U.S. Appl. No. 17/389,156 dated Apr. 16, 2024, 28 pages.
Non-Final Office Action for U.S. Appl. No. 18/630,936 mailed Jun. 13, 2024, 19 pages.
Non-Final Office Action mailed on Apr. 13, 2020, for U.S. Appl. No. 15/961,793, filed Apr. 24, 2018, 13 pages.
Non-Final Office Action mailed on Apr. 6, 2017, for U.S. Appl. No. 14/342,536, filed Jul. 30, 2014, 32 pages.
Non-Final Office Action mailed on Apr. 8, 2022, for U.S. Appl. No. 17/650,056, filed Feb. 4, 2022, 14 pages.
Non-Final Office Action mailed on Dec. 13, 2023, for U.S. Appl. No. 18/086,543, filed Dec. 21, 2022, 16 pages.
Non-Final Office Action mailed on Dec. 21, 2022, for U.S. Appl. No. 16/051,398, filed Jul. 31, 2018, 12 pages.
Non-Final Office Action mailed on Feb. 16, 2023 for U.S. Appl. No. 17/738,990, 9 pages.
Non-Final Office Action mailed on Jan. 19, 2018, for U.S. Appl. No. 14/843,926, filed Sep. 2, 2015, 11 pages.
Non-Final Office Action mailed on Jan. 26, 2024, for U.S. Appl. No. 15/913,709, filed Mar. 6, 2018, 20 pages.
Non-Final Office Action mailed on Jan. 27, 2023, for U.S. Appl. No. 17/971,415, filed Oct. 21, 2022, 15 pages.
Non-Final Office Action mailed on Jun. 2, 2023, for U.S. Appl. No. 17/367,274, filed Jul. 2, 2021, 27 pages.
Non-Final Office Action mailed on Jun. 20, 2023, for U.S. Appl. No. 17/073,331, filed Oct. 17, 2020, 10 pages.
Non-Final Office Action mailed on Mar. 10, 2016, for U.S. Appl. No. 14/965,755, filed Dec. 10, 2015, 15 pages.
Non-Final Office Action mailed on Mar. 30, 2016, for U.S. Appl. No. 14/342,536, filed Jul. 30, 2014, 31 pages.
Non-Final Office Action mailed on Mar. 9, 2017, for U.S. Appl. No. 14/965,755, filed Dec. 10, 2015, 17 pages.
Non-Final Office Action mailed on Mar. 9, 2023 for U.S. Appl. No. 17/389,156, filed Jul. 29, 2021, 24 pages.
Non-Final Office Action mailed on May 13, 2022, for U.S. Appl. No. 15/913,709, filed Mar. 6, 2018, 20 pages.
Non-Final Office Action mailed on May 2, 2023, for U.S. Appl. No. 15/913,709, filed Mar. 6, 2018, 18 pages.
Non-Final Office Action mailed on May 24, 2023, for U.S. Appl. No. 18/086,543, filed Dec. 21, 2022, 19 pages.
Non-Final Office Action mailed on May 24, 2024, for U.S. Appl. No. 18/527,128, filed Dec. 1, 2023, 17 pages.
Non-Final Office Action mailed on Nov. 1, 2017, for U.S. Appl. No. 15/687,145, filed Aug. 25, 2017, 19 pages.
Non-Final Office Action mailed on Nov. 26, 2021, for U.S. Appl. No. 16/051,398, filed Jul. 31, 2018, 15 pages.
Non-Final Office Action mailed on Nov. 29, 2021, for U.S. Appl. No. 17/389,153, filed Jul. 29, 2021, 14 pages.
Non-Final Office Action mailed on Nov. 4, 2021, for U.S. Appl. No. 16/169,939, filed Oct. 24, 2018, 20 pages.
Non-Final Office Action mailed on Oct. 16, 2020, for U.S. Appl. No. 16/051,398, filed Jul. 31, 2018, 13 pages.
Non-Final Office Action mailed on Sep. 15, 2023, for U.S. Appl. No. 16/051,398, filed Jul. 31, 2018, 12 pages.
Non-Final Office Action mailed on Sep. 16, 2020, for U.S. Appl. No. 15/913,709, filed Mar. 6, 2018, 15 pages.
Non-Final Office Action mailed on Sep. 3, 2020, for U.S. Appl. No. 16/169,939, filed Oct. 24, 2018, 19 pages.
Notice of Allowance (Corrected) mailed on Apr. 19, 2024, for U.S. Appl. No. 18/086,543, filed Dec. 21, 2022, 4 pages.
Notice of Allowance (Corrected) mailed on Jan. 25, 2024, for U.S. Appl. No. 17/349,234, filed Jun. 16, 2021, 4 pages.
Notice of Allowance (Corrected) mailed on Mar. 18, 2024, for U.S. Appl. No. 17/349,234, filed Jun. 16, 2021, 9 pages.
Notice of Allowance mailed on Apr. 10, 2024, for U.S. Appl. No. 18/086,543, filed Dec. 21, 2022, 10 pages.
Notice of Allowance mailed on Aug. 24, 2018, for U.S. Appl. No. 15/687,145, filed Aug. 25, 2017, 7 pages.
Notice of Allowance mailed on Dec. 20, 2023, for U.S. Appl. No. 17/349,234, filed Jun. 16, 2021, 13 pages.
Notice of Allowance mailed on Feb. 13, 2018, for U.S. Appl. No. 14/843,926, filed Sep. 2, 2015, 8 pages.
Notice of Allowance mailed on Jul. 12, 2017, for U.S. Appl. No. 14/342,536, filed Jul. 30, 2014, 14 pages.
Notice of Allowance mailed on Jul. 6, 2017, for U.S. Appl. No. 14/965,755, filed Dec. 10, 2015, 12 pages.
Notice of Allowance mailed on Jun. 11, 2024, for U.S. Appl. No. 15/913,709, filed Mar. 6, 2018, 9 pages.
Notice of Allowance mailed on Jun. 12, 2023, for U.S. Appl. No. 17/738,990, filed May 6, 2022, 7 pages.
Notice of Allowance mailed on Jun. 12, 2023, for U.S. Appl. No. 17/971,415, filed Oct. 21, 2022, 14 pages.
Notice of Allowance mailed on Mar. 21, 2024, for U.S. Appl. No. 18/086,543, filed Dec. 21, 2022, 6 pages.
Notice of Allowance mailed on Mar. 4, 2024, for U.S. Appl. No. 18/086,543, filed Dec. 21, 2022, 10 pages.
Notice of Allowance mailed on May 25, 2021, for U.S. Appl. No. 15/961,793, filed Apr. 24, 2018, 11 pages.
Notice of Allowance mailed on Sep. 12, 2022, for U.S. Patent Application No. 17/389, 153, filed on Jul. 29, 2021, 8 pages.
Notice of Allowance mailed on Sep. 25, 2023, for U.S. Appl. No. 17/971,415, filed Oct. 21, 2022, 8 pages.
Notice of Allowance mailed on Sep. 26, 2023, for U.S. Appl. No. 17/738,990, filed May 6, 2022, 7 pages.
Office Action and Swedish Search Report mailed on Oct. 17, 2023, for SE Application No. 2251496-2, 8 pages.
Polonsky, W.H. et al. (2011). "A survey of blood glucose monitoring in patients with type 2 diabetes: Are recommendations from health care professionals being followed?" Curr. Med. Res. & Opinion 27:31-37.
Rigla, M. et al. (2018). "Human Subcutaneous Tissue Response to Glucose Sensors: Macrophages Accumulation Impact on Sensor Accuracy," Diabetes Technology & Therapeutics 20:296-302.
Sachdeva, V. et al. (2011). "Microneedles and their applications," Recent Patents on Drug Delivery & Formulation 5:95-132.
Segel et al., "Hypoglycemia-associated autonomic failure in advanced type 2 diabetes" Diabetes Mar. 2002; 51(3):724-733.
Sharifi et al., "Redundancy in Glucose Sensing: Enhanced Accuracy and Reliability of an Electrochemical Redundant Sensor for Continuous Glucose Monitoring" Journal of Diabetes Science and Technology (2016) 10(3):669-678.
Sheikh, Z. et al. (2015). "Macrophages, Foreign Body Giant Cells and Their Response to Implantable Biomaterials," Materials 8:5671-5701.
Shi, T. et al. (2016). "Modeling and Measurement of Correlation between Blood and Interstitial Glucose Changes," J. Diab. Res. vol. 2016, 9 pages.

(56) References Cited

OTHER PUBLICATIONS

Shivers et al., "Turn it off!: diabetes device alarm fatigue considerations for the present and the future" J Diabetes Sci Technol May 1, 2013; 7(3):789-794.
Singh, T.R.R. et al. (2010). "Microporation techniques for enhanced delivery of therapeutic agents," Recent Patents on Drug Delivery & Formulation 4:1-17.
Supplementary European Search Report mailed on Oct. 9, 2023, for EP Application No. 22808101.4, 4 pages.
Swedish Search Report mailed on Feb. 3, 2023 for SE Application No. 2350067-1, 7 pages.
Tanenbaum et al., "Diabetes Device Use in Adults With Type 1 Diabetes: Barriers to Uptake and Potential Intervention Targets" Diabetes Care Feb. 2017; 40(2):181-187.
Texas Instruments (Sep. 2007). Data sheet for a LMP2234 quad micropower, 1.6V, precision, operational amplifier with CMOS input, Sep. 2007, revised Mar. 2013. 31 total pages.
Turner et al., "Intensive blood-glucose control with sulphonylureas or insulin compared with conventional treatment and risk of complications in patients with type 2 diabetes (UKPDS 33)" The Lancet (1998) Sep; 352(9131):837-853.
UK Prospective Diabetes Study (UKPDS) Group, "Intensive blood-glucose control with sulphonylureas or insulin compared with conventional treatment and risk of complications in patients with type 2 diabetes (UKPDS 33)" Lancet Sep. 12, 1998; 352(9131):837-853.
Vigersky et al., "Short- and Long-Term Effects of Real-Time Continuous Glucose Monitoring in Patients with Type 2 Diabetes" Diabetes Care Jan. 2012; 35:32-38.
Ward et al., "A Wired-Based Dual-Analyte Sensor for Glucose and Lactate: In Vitro and In Vivo Evaluation" Diabetes Technology and Therapeutics Jun. 2004; 6(3):389- 401.
Windmiller, J.R. (2012). "Molecular scale biocomputing: An enzyme logic approach," University of California, San Diego, A dissertation submitted in partial satisfaction of the requirements for the degree Doctor of Philosophy in Electrical Engineering (Photonics), 78 total pages.
Windmiller, J.R. et al. (2011). "Bicomponent microneedle array biosensor for minimally-invasive glutamate monitoring," Electroanalysis 23:2302-2309.
Windmiller, J.R. et al. (2011). "Microneedle array-based carbon paste amperometric sensors and biosensors," Analyst 136:1846-1851.
Wolicki et al., "Epidemiology and Prevention of Vaccine-Preventable Diseases: Chapter 6: Vaccine Administration" Centers for Disease Control and Prevention (2021) 17 pages.
World Health Organization, "Diabetes", Sep. 16, 2022, 5 pages.
Written Opinion of the International Search Authority mailed on Sep. 10, 2020, for PCT Application No. PCT/US2020/037379, filed on Jun. 12, 2020, 4 pages.
Written Opinion of the International Searching Authority mailed on Dec. 30, 2021, for PCT Application No. PCT/US2021/043786, filed on Jul. 29, 2021, 10 pages.
Written Opinion of the International Searching Authority mailed on Feb. 4, 2021, for PCT Application No. PCT/US2020/056517, filed on Oct. 20, 2020, 5 pages.
Written Opinion of the International Searching Authority mailed on Jun. 27, 2013, for PCT Application No. PCT/US2012/053544, filed on Aug. 31, 2012, 15 pages.
Written Opinion of the International Searching Authority mailed on Sep. 30, 2021, for PCT Application No. PCT/US2021/040385, filed on Jul. 2, 2021, 5 pages.
Yoon, Y et al. (2013). "Fabrication of a Microneedle/CNT Hierarchical Micro/Nano Surface Electrochemical Sensor and Its In-Vitro Glucose Sensing Characterization," Sensors 13:16672-16681.
Young et al., "Glucose Self-monitoring in Non-Insulin-Treated Patients With Type 2 Diabetes in Primary Care Settings: A Randomized Trial" JAMA Intern Med. Jul. 2017; 177(7):920-929.
Babity et al., "Advances in the Design of Transdermal Microneedles for Diagnostic and Monitoring Applications" Advanced Science News (2018) 14:1803186, pp. 1-16.
Bandodkar et al., "Non-invasive wearable electrochemical sensors: a review" Trends in Biotechnology Jul. 1, 2014; 32(7):363-371.
Battelino et al., "Continuous glucose monitoring and metrics for clinical trials: an international consensus statement" Lancet Diabetes Endocrinol Jan. 2023; 11:42-57.
Bollella et al., "Microneedle-Based Biosensor for Minimally-Invasive Lactate Detection" Biosens. Bioelectron. Jan. 2019; 123:152-159.
Bollella et al., "Minimally Invasive Glucose Monitoring Using a Highly Porous Gold Microneedles-Based Biosensor: Characterization and Application in Artificial Interstitial Fluid" Catalysts Jun. 2019; 9:580, pp. 1-14.
Brothers et al., "Achievements and Challenges for Real-Time Sensing of Analytes in Sweat within Wearable Platforms" Acc. Chem. Res. Jan. 2019; 52:297-306.
Burge et al., "Continuous Glucose Monitoring: The Future of Diabetes Management" Diabetes Spectr. (2008) 21:112-119.
Campbell et al., "Wearable Electrochemical Alcohol Biosensors" Curr. Opin. Electrochem. May 2018; 10:126-135.
Chinnadayyala et al., "Review-In Vivo and In Vitro Microneedle Based Enzymatic and Non- Enzymatic Continuous Glucose Monitoring Biosensors" ECS Journal of Solid State Science and Technology Apr. 2018; 7:Q3159-Q3171.
Choi et al., "Bio-Integrated Wearable Systems: A Comprehensive Review" Chem. Rev. Jan. 2019; 119:5461-5533.
Ciui et al., "Wearable Wireless Tyrosinase Bandage and Microneedle Sensors: Toward Melanoma Screening" Adv. Healthcare Mater. (2018) 7:1701264, 9 pages.
Clutter et al., "Epinephrine plasma metabolic clearance rates and physiologic thresholds for metabolic and hemodynamic actions in man" J Clin Invest. Jul. 1980; 66(1):94-101.
Coffey et al., "Rapid and selective sampling of IgG from skin in less than 1 min using a high surface area wearable immunoassay patch" Biomaterials Mar. 2018; 170:49-57.
Cui et al., "Effect of Pre-treatment on the Surface and Electrochemical Properties of Screen-printed Carbon Paste Electrodes" Analyst Aug. 2001; 126(8):1399-1403.
Czupryniak et al., "Ambulatory Glucose Profile (AGP) Report in Daily Care of Patients with Diabetes: Practical Tips and Recommendations" Diabetes Ther Apr. 2022; 13:811-821.
Darmau et al., "Self-Extracting Dextran-Based Hydrogel Microneedle Arrays with an Interpenetrating Bioelectroenzymatic Sensor for Transdermal Monitoring with Matrix Protection", e2403209, 17 pages, Jan. 2025; 14(2).
Donnelly et al., "Microneedle Arrays Allow Lower Microbial Penetration Than Hypodermic Needles In Vitro" Pharmaceutical Research Nov. 2009; 26(11):2513- 2522.
Dunn et al., "Wearables and the medical revolution" Per. Med. Sep. 2018; 15:429-448.
Eddy et al., "The modification of enzyme electrode properties with non-conducting electropolymerised films" Biosensors & Bioelectronics (1995) 10:831-839.
El-Laboudi et al., "Use of Microneedle Array Devices for Continuous Glucose Monitoring: A Review" Diabetes Technology & Therapeutics (2013) 15(1):101-115.
EP Application No. 25191106.1, Extended European Search Report mailed Nov. 26, 2025; Applicant Biolinq, Inc; 8 pages.
EP Application No. 25221877.1, Extended European Search Report mailed Jan. 20, 2026; Applicant Biolinq Incorporated; 11 pages.
EP Application No. 25151041.8, Extended European Search Report mailed May 27, 2025; Applicant Biolinq, Inc; 7 pages.
Fayfman et al., "Management of Hyperglycemic Crises: Diabetic ketoacidosis and hyperglycemic hyperosmolar state" Med Clin North Am. May 2017; 101(3):587-606.
U.S. Appl. No. 17/073,331, Final Office Action mailed Dec. 17, 2024, Inventor: Windmiller et al.; 13 pages.
U.S. Appl. No. 17/650,056, Final Office Action mailed on Feb. 14, 2025, Inventor: Wang et al.; 34 pages.
U.S. Appl. No. 18/527,128, Final Office Action mailed Sep. 6, 2024, Inventor: Windmiller et al.; 19 pages.

(56) References Cited

OTHER PUBLICATIONS

U.S. Appl. No. 18/630,936, Final Office Action mailed Sep. 20, 2024, Inventor: Tangney et al.; 16 pages.
U.S. Appl. No. 17/650,056, Final Office Action mailed on Jul. 15, 2022, Inventor: Wang et al.; 25 pages.
U.S. Appl. No. 17/650,056, Final Office Action mailed on Sep. 7, 2023, Inventor: Wang et al.; 29 pages.
Gao et al., "Simultaneous detection of glucose, uric acid and cholesterol using flexible microneedle electrode array-based biosensor and multi-channel portable electrochemical analyzer" Sensors and Actuators B: Chemical (2019) 287:102-110.
Garcia-Lopez et al., "Study of the fabrication of AISI 316L microneedle arrays" Procedia Manufacturing (2018) 26:117-124.
Ghimire et al., "Ketoacidosis" StatPearls Publishing, Jan. 2024, NCBI Bookshelf, 8 pages.
Goud et al., "Wearable Electrochemical Microneedle Sensor for Continuous Monitoring of Levodopa: Toward Parkinson Management" ACS Sens. Aug. 2019; 4:2196-2204.
Gowers et al., "Development of a Minimally Invasive Microneedle-Based Sensor for Continuous Monitoring of β-Lactam Antibiotic Concentrations in Vivo" ACS Sens. Apr. 2019; 4:1072- 1080.
Heikenfeld et al., "Accessing Analytes in Biofluids for Peripheral Biochemical Monitoring" Nat. Biotechnol. Apr. 2019; 37:407-419.
Heikenfeld et al., "Wearable sensors: modalities, challenges, and prospects" Lab Chip Jan. 2018; 18:217-248.
Heinemann, "Interferences With CGM Systems: Practical Relevance?" Journal of Diabetes Science and Technology Mar. 2022; 16(2) 271-274.
Henry et al. "Microfabricated microneedles: a novel approach to transdermal drug delivery." Journal of Pharmaceutical Sciences. Aug. 1998; 87(8):922-925.
Ingrole et al., "Trends of microneedle technology in the scientific literature, patents, clinical trials and internet activity" Biomaterials (2021) 267:120491, pp. 1-24.
PCT Application No. PCT/US2024/014324, International Preliminary Report on Patentability mailed Aug. 14, 2025; Applicant Biolinq, Inc; 14 pages.
PCT Application No. PCT/US2024/014324, International Search Report and Written Opinion mailed Sep. 20, 2024, Applicant Biolinq, Inc; 22 pages.
PCT Application No. PCT/US2022/028196, International Search Report mailed on Aug. 29, 2022; Applicant Biolinq, Inc; 2 pages.
Jiang et al., "Microneedle-based skin patch for blood-free rapid diagnostic testing" Microsystems and Nanoengineering (2020) 6:96, pp. 1-11.
Kathuria et al., "Polymeric Microneedle Array Fabrication by Photolithography" Journal of Visualized Experiments Nov. 2015; 105:e52914, pp. 1-8.
Kim et al., "Continuous glucose monitoring using a microneedle array sensor coupled with a wireless signal transmitter" Sensors & Actuators: B. Chemical (2019) 281:14-21.
Kim et al., "Wearable Biosensors for Healthcare Monitoring" Nat. Biotechnol. Apr. 2019; 37(4):389-406.
Lee et al., "A Graphene-Based Electrochemical Device with Thermoresponsive Microneedles for Diabetes Monitoring and Therapy" Nat. Nanotechnol. Mar. 2016; 11:566-572.
Lee et al., "A Patch Type Non-Enzymatic Biosensor Based on 3D Sus Micro-Needle Electrode Array for Minimally Invasive Continuous Glucose Monitoring" Sensors Actuators B Chem. (2016) 222:1144-1151.
Lee et al., "Continuous glucose monitoring systems - Current status and future perspectives of the flagship technologies in biosensor research" Biosens. Bioelectron. Feb. 2021; 181:113054, 19 pages.
Liu et al., "Microneedles for transdermal diagnostics: Recent advances and new horizons" Biomaterials (2020) 232:119740, pp. 1-16.
Maahs et al., "Effect of Acetaminophen on CGM Glucose in an Outpatient Setting" Diabetes Care Oct. 2015; 38:e158-e159.
Madden et al., "Biosensing in dermal interstitial fluid using microneedle based electrochemical devices" Sensing and Bio-Sensing Research (2020) 29:100348, 1-17.
Miller et al., "Microneedle-Based Sensors for Medical Diagnosis" J. Mater. Chem. B Feb. 2016; 4:1379-1383.
Miller et al., "Multiplexed microneedle-based biosensor array for characterization of metabolic acidosis" Talanta (2012) 88:739-742.
Min et al., "Wearable electrochemical biosensors in North America" Biosensors and Bioelectronics Jan. 2021; 172:112750, pp. 1-16.
Muller et al., "Surface Modified Microprojection Arrays for the Selective Extraction of the Dengue Virus NS1 Protein As a Marker for Disease" Anal. Chem. Mar. 2012; 84:3262-3268.
Nguyen et al., "Human studies with microneedles for evaluation of their efficacy and safety" Expert Opinion on Drug Delivery Mar. 2018; 15(3):235-245.
U.S. Appl. No. 16/051,398, Non-Final Office Action mailed Feb. 20, 2025, Inventor: Windmiller et al.; 13 pages.
U.S. Appl. No. 17/073,331, Non-Final Office Action mailed Aug. 28, 2024, Inventor: Windmiller et al.; 13 pages.
U.S. Appl. No. 17/389,156, Non-Final Office Action mailed Jan. 22, 2025, Inventor: Windmiller et al.; 17 pages.
U.S. Appl. No. 17/757,216, Non-Final Office Action mailed on Mar. 26, 2025, Inventor: Wang et al.; 14 pages.
U.S. Appl. No. 18/431,808, Non-Final Office Action mailed Nov. 27, 2024, Inventor: Windmiller et al.; 16 pages.
U.S. Appl. No. 18/630,936, Non-Final Office Action mailed on Dec. 12, 2024, Inventor: Tangney et al.; 18 pages.
U.S. Appl. No. 18/824,598, Non-Final Office Action mailed Nov. 4, 2024, Inventor: Windmiller et al.; 14 pages.
U.S. Appl. No. 18/824,598, Non-Final Office Action mailed on Dec. 23, 2024, Inventor: Windmiller et al.; 27 pages.
U.S. Appl. No. 18/926,029, Non-Final Office Action mailed on Dec. 12, 2024, Inventor: Windmiller et al.; 10 pages.
U.S. Appl. No. 17/650,056, Non-Final Office Action mailed on Jul. 30, 2024, Inventor: Wang et al.; 32 pages.
U.S. Appl. No. 17/650,056, Non-Final Office Action mailed on Mar. 29, 2023, Inventor: Wang et al.; 27 pages.
U.S. Appl. No. 17/389,156, Notice of Allowance mailed Dec. 27, 2024, Inventor: Windmiller et al.; 6 pages.
U.S. Appl. No. 17/389,156, Notice of Allowance mailed Nov. 20, 2024, Inventor: Windmiller et al.; 5 pages.
U.S. Appl. No. 18/431,808, Notice of Allowance mailed Feb. 20, 2025, Inventor: Windmiller et al.; 7 pages.
U.S. Application No. 18/527, 128, Notice of Allowance mailed Feb. 26, 2025, Inventor: Windmiller et al.; 9 pages.
U.S. Appl. No. 18/824,598, Notice of Allowance mailed Apr. 4, 2025, Inventor: Windmiller et al.; 9 pages.
U.S. Appl. No. 18/926,029, Notice of Allowance mailed Mar. 5, 2025, Inventor: Windmiller et al.; 8 pages.
Ohashi et al., "Analgesic Effect of Acetaminophen: A Review of Known and Novel Mechanisms of Action" Front Pharmacol. Nov. 30, 2020;11:580289, 6 pages.
Parrilla et al., "Wearable All-Solid-State Potentiometric Microneedle Patch for Intradermal Potassium Detection" Analytical Chemistry Jan. 2019; 91:1578-1586.
Prausnitz, "Engineering Microneedle Patches for Vaccination and Drug Delivery to Skin" Annu. Rev. Chem. Biomol. Eng. Jun. 2017; 8:177-200.
Rawson et al., "Microneedle biosensors for real-time, minimally invasive drug monitoring of phenoxymethylpenicillin: a first-in-human evaluation in healthy volunteers" Lancet Digital Health Nov. 2019; 1:e335-e343.
Rawson et al., "Towards a minimally invasive device for beta-lactam monitoring in humans" Electrochem Commun. Sep.2018; 82:1-12.
Samant et al., "Mechanisms of sampling interstitial fluid from skin using a microneedle patch," Pnas USA May 2018; 115(8):4583-4588.
Sharma et al., "A pilot study in humans of microneedle sensor arrays for continuous glucose monitoring" Analytical Methods Mar. 2018; 10:2088-2095.
Sharma et al., "Evaluation of a minimally invasive glucose biosensor for continuous tissue monitoring" Anal Bioanal Chem Oct. 2016; 408:8247-8435, 9 pages.

(56) References Cited

OTHER PUBLICATIONS

Sharma et al., "Rapid, low cost prototyping of transdermal devices for personal healthcare monitoring" Sens Biosensing Res. Apr. 2017; 13:104-108.
Sulaiman et al., "Hydrogel-Coated Microneedle Arrays for Minimally Invasive Sampling and Sensing of Specific Circulating Nucleic Acids from Skin Interstitial Fluid" ACS Nano Aug. 2019; 13:9620-9628.
Takeuchi et al., "Functionalized microneedles for continuous glucose monitoring" Nano Convergence (2018) 5:28, pp. 1-10.
Tasca et al., "Microneedle-based electrochemical devices for transdermal biosensing: a review" Electrochemistry Apr. 2019; 16:42-49.
Tehrani et al., "An integrated wearable microneedle array for the continuous monitoring of multiple biomarkers in interstitial fluid" Nature Biomedical Engineering Nov. 2022; 6(11):1214-1224.
Teymourian et al., "Electrochemical glucose sensors in diabetes management: an updated review (2010-2020)" Royal Society of Chemistry, Chem. Soc. Rev. (2020) 49:7671-7709.
Teymourian et al., "Lab under the Skin: Microneedle Based Wearable Devices" Adv. Healthc. Mater. (2021) 10:2002255, 19 pages.
Teymourian et al., "Microneedle-Based Detection of Ketone Bodies along with Glucose and Lactate: Toward Real-Time Continuous Interstitial Fluid Monitoring of Diabetic Ketosis and Ketoacidosis" Anal. Chem. (2020) 92:2291-2300.
Teymourian et al., "Wearable Electrochemical Sensors for the Monitoring and Screening of Drugs" ACS Sensors Aug. 2020; 5:2679-2700.
U.S. Appl. No. 16/051,398, Notice of Allowance mailed Dec. 4, 2025; Inventor: Windmiller et al.; 10 pages.
U.S. Appl. No. 17/073,331, Final Office Action mailed Feb. 6, 2026; Inventor Windmiller et al.; 18 pages.
U.S. Appl. No. 17/073,331, Non-Final Office Action mailed Jul. 16, 2025; Inventor Windmiller et al.; 21 pages.
U.S. Appl. No. 17/389,156, Final Office Action mailed Oct. 21, 2025; Inventor Windmiller et al.; 18 pages.
U.S. Appl. No. 17/650,056, Non-Final Office Action mailed Sep. 5, 2025; Inventor Wang et al.; 29 pages.
U.S. Appl. No. 17/757,216, Notice of Allowance mailed Nov. 7, 2025; Inventor Wang et al.; 13 pages.
U.S. Appl. No. 18/050,450, Non-Final Office Action mailed Aug. 13, 2025; Inventor MallireS et al.; 9 pages.
U.S. Appl. No. 18/510,544, Non-Final Office Action mailed Feb. 25, 2026; Inventor Windmiller, Joshua Ray et al.; 12 pages.
U.S. Appl. No. 18/630,936, Notice of Allowance mailed Jul. 1, 2025; Inventor Tangney et al.; 8 pages.
U.S. Appl. No. 19/213,907, Non-Final Office Action mailed Aug. 8, 2025; Inventor Campbell et al.; 12 pages.
U.S. Appl. No. 19/213,907, Notice of Allowance mailed Jan. 21, 2026; Campbell et al.; 7 pages.
U.S. Appl. No. 19/258,472, Non-Final Office Action mailed Aug. 12, 2025; Inventor Windmiller et al.; 29 pages.
U.S. Appl. No. 19/258,472, Notice of Allowance mailed Dec. 17, 2025; Inventor Windmiller et al.; 9 pages.
U.S. Appl. No. 19/347,553, Non-Final Office Action mailed Feb. 25, 2026; Inventor Campbell et al.; 20 pages.
Valdes-Ramirez et al., "Microneedle-Based Self-Powered Glucose Sensor" Electrochem. Commun. Jul. 2014; 47:58-62.
Ventrelli et al., "Microneedles for Transdermal Biosensing: Current Picture and Future Direction" Adv. Healthcare Mater. (2015) 4:2606-2640.
Vicente-Perez et al., "Repeat application of microneedles does not alter skin appearance or barrier function and causes No. measurable disturbance of serum biomarkers of infection, inflammation or immunity in mice in vivo" European Journal of Pharmaceutics and Biopharmaceutics Aug. 2017; 117:400-407.
Wang, "Electrochemical Glucose Biosensors" Chemical Reviews (2008) 108:814- 825.
Wang et al., "Microneedle patch for the ultrasensitive quantification of protein biomarkers in interstitial fluid" Nature Biomedical Engineering Jan. 2021; 5:64-76.
Wang et al., "Recent Advances in the Design of Polymeric Microneedles for Transdermal Drug Delivery and Biosensing" Lab Chip Mar. 2017; 17:1373-1387.
Wei et al. "Integrated individually addressable microneedle arrays for robust glucose monitoring and on demand insulin releasing." 12 pages on Nov. 11; 11(1):211, 2025.
Wiorek et al., "Epidermal Patch with Glucose Biosensor: pH and Temperature Correction toward More Accurate Sweat Analysis during Sport Practice" Anal. Chem. Jun. 2020; 92:10153-10161.
Wolkowicz et al., "A Review of Biomarkers in the Context of Type 1 Diabetes: Biological Sensing for Enhanced Glucose Control" Bioeng. Transl. Med. (2021) 6(2):e10201, 17 pages.
World Economic Forum, "Top 10 Emerging Technologies of 2020" Special Report Nov. 2020, 26 pages.
Xie et al., "Engineering Microneedles for Therapy and Diagnosis: A Survey" Micromachines Mar. 2020; 11:271, pp. 1-28.
Xie et al., "Reduction of measurement noise in a continuous glucose monitor by coating the sensor with a zwitterionic polymer" Nature Biomedical Engineering Dec. 2018; 2:894-906, 15 pages.
Yang et al., "In Situ Sampling and Monitoring Cell-Free DNA of the Epstein-Barr Virus from Dermal Interstitial Fluid Using Wearable Microneedle Patches" ACS Applied Materials & Interfaces Sep. 2019; 11:38448-38458.
Yetisen et al., "Wearables in Medicine" Adv. Mater. Jun. 2018; 30:1706910, 26 pages.
Yue et al., "Evaluation of a 12-Hour Sustained-Release Acetaminophen (Paracetamol) Formulation: A Randomized, 3-Way Crossover Pharmacokinetic and Safety Study in Healthy Volunteers" Clinical Pharmacology in Drug Development Jan. 2018; 7(1):95-101.
Zhang et al., "Bio-inspired clamping microneedle arrays from flexible ferrofluid- configured moldings" Science Bulletin Jun. 2019; 64:1110-1117.
Zhang et al., "Encoded Microneedle Arrays for Detection of Skin Interstitial Fluid Biomarkers" Advanced Materials Jul. 2019; 31:1902825, pp. 1-8.
Zhang et al., "Microneedle-assisted technology for minimally invasive medical sensing" Microchemical Journal (2021) 162:105830, pp. 1-12.

* cited by examiner

HETEROGENEOUS INTEGRATION OF SILICON-FABRICATED SOLID MICRONEEDLE SENSORS AND CMOS CIRCUITRY

CROSS REFERENCE TO RELATED APPLICATIONS

This application is a continuation of U.S. patent application Ser. No. 17/349,234, filed on Jun. 16, 2021, which is a continuation application of U.S. patent application Ser. No. 15/961,793, filed on Apr. 24, 2018, now U.S. Pat. No. 11,045,142, which claims priority to U.S. Provisional Patent Application No. 62/492,142, filed on Apr. 29, 2017, now expired, the contents of each of which are hereby incorporated by reference in their entirety.

STATEMENT REGARDING FEDERALLY SPONSORED RESEARCH OR DEVELOPMENT

Not Applicable

BACKGROUND OF THE INVENTION

Field of the Invention

The present invention generally relates to sensors.

Description of the Related Art

The integration of silicon-fabricated microneedles with conventional silicon complementary metal-oxide semiconductor ("CMOS") circuitry is of utmost importance in perpetuating the miniaturization efforts of body-worn medical devices. Despite the current state of semiconductor miniaturization and packaging, the creation of a heterogeneous system comprised of microneedle-based sensors and the CMOS circuitry required to transduce the signals generated by such devices has posed a formidable challenge to those aiming to create low-profile, highly-integrated body-worn sensors for the quantification of physiological or biochemical signals. Indeed, leveraging state-of-the-art semiconductor processing and packaging methods in conjunction with CMOS-based circuitry and recent developments in minimally-invasive silicon-based microneedle devices for physiological and biochemical sensing would enable the construction of a self-contained sensing system in a single package.

U.S. Pat. No. 8,506,529 for a Method and structure of monolithetically integrated microneedle biochip discloses a method and device using CMOS and MEMS fabrication techniques for making an integrated microneedle device with integrated circuits. Merely by way of example, the technology can be applied to bio and chemical sensing, and other bioMEMS applications. In some embodiments, the integrated circuits are completed using standard IC processes. For example, an array of microneedles are fabricated on top of the IC substrate followed by formation of micro fluidic channels in the substrate. On-chip integrated circuits enable real-time sensing and intelligent drug delivery.

U.S. Pat. No. 5,953,306 for a Micro needle probe apparatus having probes cantilevered over respective electronic circuits, moving medium memory device including same and method of making same discloses micro needle probe apparatus that includes a probe and its associated electronic circuit. The electronic circuit is formed in a substrate and includes at least one metal interconnection layer. The probe is cantilevered over the electronic circuit and is composed of a metal probe arm, a support post that anchors one end of the probe arm to the substrate, and a micro needle mounted adjacent the moveable end of the probe arm. The probe apparatus may be used as the read/write mechanism of the moving-medium type memory device.

U.S. Pat. No. 8,452,369 for a CMOS compatible microneedle structures discloses an electronic device for sensing and/or actuating, the electronic device comprising at least one microneedle (10) on a substrate (1), each of the microneedles (10) comprising at least one channel (7, 8) surrounded by an insulating layer (6).

Prior art solutions have been concerned with the integration of silicon-based microneedle arrays and CMOS circuitry as discrete devices populating a printed circuit board; in certain circumstances, these metallic wires are coated with a layer of metal salt, such as a silver wire functionalized on the surface with a layer of silver chloride. Such integration fails to minimize device footprint, especially in x-y dimensions, since device area constitutes the summation of the area of any discrete CMOS circuitry, microneedle sensor (s), and area devoted to interconnect between these two entities on said printed circuit board. Under such a design philosophy, efforts have largely been devoted to ultra-large scale integration of CMOS circuitry and the creation of CMOS systems-on-a-chip to minimize the number of discrete CMOS devices populating a sensing system. Likewise, recent efforts have been directed at reducing the number of components required to realize microneedle-mediated sensing via the integration of electrophysiological and electrochemical sensors on self-contained solid microneedle devices, thereby obviating the need for separate hollow microneedle-based lumens for physiological fluid extraction and an adjoining chamber for which the chemical reaction and/or electrochemical detection are intended to occur. The heterogeneous integration of CMOS- and microneedle-based capabilities into a single package would facilitate a novel means to the construction of self-contained sensor-transducer devices that require substantially less footprint than conventional discrete constituents that comprise current body-worn sensing systems can provide.

BRIEF SUMMARY OF THE INVENTION

The technology described herein relates to methods of integration and packaging of heterogenous semiconductor substrates.

One aspect of the present invention is a skin-adorned physiological or biochemical sensing system. The system comprises a first substrate and a second substrate. The first substrate features an anterior and a posterior surface. The first substrate comprises an array of solid microneedles on the anterior surface designed to penetrate a biological interface to access a physiological fluid or tissue. Each microneedle contains an addressable metal electrode located on the surface of the microneedle which is in electrical communication with a metal surface located on the posterior surface of the first substrate by means of a conductive conduit, to form a sensor component capable of electrical interface with the physiological fluid or tissue. The second substrate has an anterior and a posterior surface. The second substrate comprises integrated circuitry on the anterior surface designed to transduce at least one signal produced by an electrophysiological or electrochemical reaction occurring at the metal electrode, to form a transducer component. The posterior surface of the first substrate is stacked to the anterior surface of the second substrate. The first substrate is bonded to the second substrate to create an electrical interconnect between the first substrate and the second substrate. A sensing system is formed that is capable of interpreting the signal arising from the electrophysiological or electrochemical reaction to ascertain the level of some physiological or biochemical entity.

Yet another aspect of the present invention is a method for the heterogeneous and monolithic integration of a semiconductor-based solid microneedles sensor and a semiconductor-based CMOS circuitry transducer. The method includes bonding a plurality of pads located on the posterior surface of sensor to a plurality of pads on either the anterior or posterior surface of a transducer to facilitate electrical communication between a sensor and the transducer. The sensor comprises a plurality of solid microneedles on the anterior surface of a substrate, each of the plurality of microneedles comprising an addressable sensing electrode. The transducer comprises a potentiostat, an analog front end, an amplifier, a filter, an analog-to-digital converter, microcontroller, and a wireless radio; Each of the plurality of sensing electrodes is accessible on a posterior surface of the substrate by means of a plurality of vertically-oriented conducting channels, wherein at a location on the posterior surface in which each of plurality of vertically-oriented conducting channels exit from the substrate. A plurality of conductive pads are positioned to facilitate bonding to the surface of a second substrate.

Yet another aspect of the present invention is a method for the heterogeneous and monolithic integration of a semiconductor-based solid microneedles sensor and a semiconductor-based CMOS circuitry transducer. The method includes mating a first substrate to a second substrate such that a posterior surface of the first substrate is bonded to an anterior surface of the second substrate. The first substrate contains a transducer and the second substrate containing a sensor. The sensor comprises a plurality of solid microneedles on the anterior surface of a substrate. Each of the plurality of microneedles comprises an addressable sensing electrode. The transducer comprises a potentiostat, an analog front end, an amplifier, a filter, an analog-to-digital converter, microcontroller, and a wireless radio. Each of the plurality of sensing electrodes is accessible on a posterior surface of the substrate by means of a plurality of vertically-oriented conducting channels, wherein at a location on the posterior surface in which each of plurality of vertically-oriented conducting channels exit from the substrate. A plurality of conductive pads are positioned to facilitate bonding to the surface of a second substrate.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
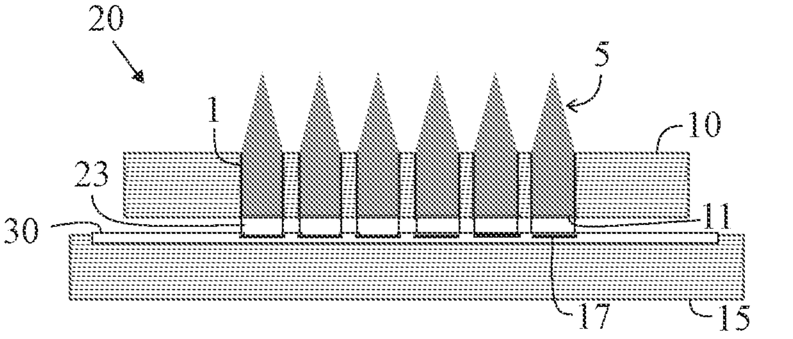
FIG. 1 is a diagrammatic representation of a die stack with CMOS circuitry on anterior surface of a second die.

To facilitate increased patient compliance and improve the treatment of acute or chronic disease, body-adorned medical devices such as non-invasive sensor patches as well as minimally-invasive subcutaneously- and intracutaneously-implanted sensors have substantially expanded in use over the past decade. Much of this proliferation has been a result of advancements in electrochemical sensor technology, which enables the quantification of circulating analytes in physiological fluids (blood, interstitial fluid, etc.) in miniaturized and compact platforms. These platforms, which integrate the sensor and transducer constituents into a single device, have been applied to such embodiments as continuous glucose monitoring. Although the current state-of-the-art has resulted in the widespread utilization of body-worn devices in the healthcare domain, the realization of truly low-profile and potentially skin-conformal skin-adorned or skin-adhered medical devices remains elusive as current limitations with electronic device packaging often entails the mounting and interconnect, in a 2-dimensional fashion, of discrete components populating a printed circuit board.

The present invention is a method for the three-dimensional ("3D") packaging and interconnection of heterogeneous, semiconductor-based systems for body-worn health and wellness devices, such as MEMS-fabricated microneedle arrays and CMOS-based transducers. One aspect of the present invention is a novel method of die attaching via stacking and interconnection of CMOS- and MEMS-based dies as a means to achieve 2.5D or 3D integration. Another aspect of the present invention is a method of fabricating CMOS and MEMS systems on geographically distinct regions of a shared surface of substrate whereby said systems are interconnected to one another by means of conductive traces or through-silicon vias. Another aspect of the present invention is a method of fabricating CMOS and MEMS on opposing surfaces of a substrate whereby interconnect between the two systems is facilitated by through-silicon vias. The ability to perform MEMS-to-CMOS packaging via stacked wire-bonding, reflow soldering of solder balls, or stud-bumping in conjunction with silicon or epoxy interposers enables the construction of vertically-integrated 2.5- or 3-dimensional self-contained sensing systems. Likewise, co-substrate integration of microneedles and CMOS circuitry represents another compelling solution enabled by through-silicon vias (TSVs), flip-chip bonding techniques, or a combination of these capabilities.

The monolithic integration of CMOS-based circuitry and microneedle-based transducers solves several noteworthy challenges confronting those developing technologies in the medical devices and wearable sensors domains. The present invention represents a novel approach to facilitating the synthesis of a heterogeneous, self-contained sensor-transducer system that addresses the shortcomings of the prior art while remaining amenable to highly scalable manufacturing processes.

These prior art shortcomings include the following:

(1) The necessity of interconnect of distinct microneedle-based sensors and CMOS-based transducers, as required for the readout of said microneedles, by means of integration as discrete packaged and mounted/bonded devices populating a printed circuit board: Limitation: A printed circuit board containing discrete microneedle and CMOS systems cannot be easily miniaturized beyond the xy-dimensions associated with said systems as well as the interconnects between the two, thereby placing a technological barrier to the realization of miniaturized skin-worn sensor devices. Moreover, routing electrical connections between two or more such discrete systems on a printed circuit board imposes added constraints of complexity and cost. Mitigation: The utilization of advanced semiconductor processing and packaging techniques facilitates the creation of 2.5- or 3-dimensional, self-contained microneedle-CMOS sensor-transducer systems or heterogeneously integrated microneedle-CMOS architectures sharing a common substrate.

(2) The interconnect of discrete microneedle-based sensors and CMOS-based transducers using conventional PCB traces: Limitation: Interconnect of distinct microneedle and CMOS systems on a printed circuit board is not amenable to maintaining signal fidelity, especially when such signals are analog in nature and reside in the nanoampere/microvolt (or lower) range. Mitigation: As the spatial extent of the interconnect between two electronic systems is directly proportional to noise ingress, the co-location of microneedle and CMOS systems on a shared substrate or the interconnect of said systems by means of solder balls/wire bonds serves to minimize the distance over which said systems interact and hence the noise imparted in the combined system. By reducing interconnect length between the microneedle sensor and CMOS transducer, the chief source of electronic noise and signal degradation is thus minimized.

(3) Inability to scale heterogeneous microneedle- and CMOS-based systems to dimensions enabling unobtrusive, conformal, and flexible skin-adorned medical patches: Limitation: Owing to their disparate manufacturing and packaging requirements, silicon micro-fabricated microneedles and CMOS circuitry have conventionally been packaged as mutually-exclusive, discrete entities populating a printed circuit board. Indeed, heterogeneous integration in a single package or on a single substrate presents difficulty owing to incompatibilities in manufacturing processes and packaging requirements. Mitigation: Employing a monolithic approach to microneedle and CMOS integration, either by means of co-locating the said constituents on the same substrate, or packaging the components as a single stacked entity, heralds the realization of highly miniaturized, self-contained sensing systems capable of direct integration into skin-adorned medical patches characterized by low footprint.

The technology disclosed herein specifies methods to achieve the heterogeneous and monolithic integration of semiconductor-based solid microneedles sensor and the semiconductor-based CMOS circuitry transducer required to interpret readings from the sensor. The sensor preferably contains one or a plurality of solid microneedles on an anterior surface of a substrate, each containing an addressable sensing electrode. The sensor is preferably designed to penetrate a biological interface to access a physiological fluid or tissue. The transducer preferably contains one or a plurality of integrated circuits using complementary metal oxide semiconductor (CMOS) technology. The transducer is preferably designed to control the sensor by applying a specific signal or stimulus to the sensor as well as interpreting the resulting electrical response of the sensor to the signal or stimulus. The transducer preferably includes at least one of the following components: a potentiostat, an analog front end, an amplifier, a filter, an analog-to-digital converter, microcontroller, and a wireless radio. Three approaches may be leveraged to achieve this aim of heterogeneous integration of the sensor and the transducer.

The stacked substrate 10: The sensing electrodes are accessible on the opposing (posterior) surface of the substrate by means of vertically-oriented conducting channels known as through-substrate vias (TSVs), and as described in more detail in Windmiller, et al., U.S. patent application Ser. No. 15/913,709, filed on Mar. 6, 2018, for Methods For Achieving An Isolated Electrical Interface Between An Anterior Surface Of A Microneedle Structure And A Posterior Surface Of A Support Structure is hereby incorporated by reference in its entirety. At a location on a posterior surface in which the TSVs exit from the substrate, conductive pads are found to facilitate bonding to the surface of a second substrate. The conductive pads are preferably located on the posterior surface of the sensor, and are bonded to conductive pads on either the anterior or posterior surface of the transducer to facilitate an electrical communication between the sensor and the transducer. Bonding is achieved by at least one of: stud bumps, solder balls, direct bonding, surface activated bonding, plasma activated bonding, fusion bonding, metal layer bonding, anodic bonding, eutectic bonding, glass frit bonding, insulating layer bonding, adhesive bonding, thermocompression bonding, reactive bonding, transient liquid phase diffusion bonding, physical bonding, and chemical bonding. Optionally, the sensor and the transducer may be wire-bonded to achieve electrical interface between the two systems. Optionally, the transducer (following mating with the sensor) may be mated, in a similar fashion as above, to another CMOS-containing substrate. Optionally, the transducer (following mating with the sensor) may be wire-bonded or stud-bumped and soldered to a printed circuit board to enable electrical communication with discrete electrical or electronic devices such as, but not limited to, batteries, antennas, resistors, capacitors, inductors, diodes, transistors, and discrete semiconductor components.

The Co-Substrate Integration: The sensing electrodes are accessible on the opposing (posterior) surface of the substrate by means of vertically-oriented conducting channels known as through-substrate vias (TSVs). At a location on the posterior surface in which the TSVs exit from the substrate, conductive traces are found to route signals generated by the sensor to the transducer to facilitate an electrical communication between the sensor located on the anterior surface of substrate and the transducer located on the posterior surface of substrate. Optionally, the substrate (hereinafter referred to as the first substrate) may be mated to another CMOS-containing substrate (second substrate) such that the posterior surface of the first substrate (containing the transducer) is bonded to the anterior surface of the second substrate by means of at least one of: stud bumps, solder balls, direct bonding, surface activated bonding, plasma activated bonding, fusion bonding, metal layer bonding, anodic bonding, eutectic bonding, glass frit bonding, insulating layer bonding, adhesive bonding, thermocompression bonding, reactive bonding, transient liquid phase diffusion bonding, physical bonding, and chemical bonding. Optionally, the first substrate or the second substrate (if present) may be wire-bonded or stud-bumped and soldered to a printed circuit board to enable electrical communication with discrete electrical or electronic devices such as, but not limited to, batteries, antennas, resistors, capacitors, inductors, diodes, transistors, and discrete semiconductor components.

The Co-Planar Integration: The sensing electrodes are accessible on the same (anterior) surface of the substrate by means of horizontally-oriented conducting traces. The conductive traces route electrical signals generated by sensor to the transducer to facilitate an electrical communication between the sensor and the transducer, both co-located on spatially distinct regions on the anterior surface of the substrate. Optionally, the substrate (hereinafter referred to as the first substrate) may be mated to another CMOS-containing silicon die (second substrate) such that the posterior surface of the first substrate is bonded to the anterior surface of the second substrate by means of at least one of: stud bumps, solder balls, direct bonding, surface activated bonding, plasma activated bonding, fusion bonding, metal layer bonding, anodic bonding, eutectic bonding, glass frit bonding, insulating layer bonding, adhesive bonding, thermocompression bonding, reactive bonding, transient liquid phase diffusion bonding, physical bonding, and chemical bonding. Optionally, the first substrate or the second substrate may be wire-bonded or stud-bumped and soldered to a printed circuit board to enable electrical communication with discrete electrical or electronic devices such as, but not limited to, batteries, antennas, resistors, capacitors, inductors, diodes, transistors, and discrete semiconductor components.

Under each of the above scenarios, the substrate may comprise a semiconductor wafer or die selected from one of the Group IV elements (i.e. Silicon, Germanium), the Group VI elements (i.e. Selenium, Tellurium), composites comprising II-VI elements (i.e. Cadmium Sulfide, Zinc Oxide), and composites comprising III-V elements (i.e. Gallium Arsenide, Indium Phosphide); the TSV may comprise the doped or intrinsically conducting species of the above materials as well as a metal.

The microneedle sensor 5 breaches a biological interface to access a physiological fluid or tissue. The microneedle sensor 5 contains one or a plurality of solid microneedles on the anterior surface of a silicon substrate 10, each of the microneedle constituents contain an addressable sensing electrode in physical contact with the physiological fluid or tissue. In addition, the sensing electrode(s) are in direct electrical communication either with another region on the anterior surface of the silicon substrate (by means of metallic traces/conduits) or on the posterior surface of the substrate (by means of through-silicon vias 1). The microneedle sensor 5 is designed to stimulate, sustain, and provide a means to read out some electrophysiological or electrochemical signal or reaction at the electrode surface.

The CMOS transducer 30 converts some variations in electrophysiological or electrochemical quantities arising at the interface of the microneedle sensor 5 and the biological interface into an electrical signal or vice versa. The CMOS transducer 30 transduces the signal(s) produced by the microneedle sensor 5 to information capable of being interpreted to ascertain the level of some physiological or biochemical entity. The CMOS transducer 30 contains complementary metal oxide semiconductor circuitry, patterned on a silicon substrate, to implement at least one of the following functionalities: a potentiostat, an analog front end, an amplifier, a filter, an analog-to-digital converter, microcontroller, and a wireless radio. Optionally the CMOS transducer 30 can control the microneedle sensor 5 by applying a certain potential, current, or frequency-modulated signal while simultaneously quantifying the electrical response of the microneedle sensor 5. Optionally the CMOS transducer 30 can perform processing on the signal to mitigate noise and can feature a wireless capability to relay said raw or processed signal to another device. Optionally the CMOS transducer 30 can interface with a display to present the user with sensor readings.

The semiconductor substrates 10 provide a mechanical support for the implementation of sensor and transducer constituents. The semiconductor substrates 10 are comprised of a semiconductor wafer or die selected from one of the Group IV elements (i.e. Silicon, Germanium), the Group VI elements (i.e. Selenium, Tellurium), composites comprising II-VI elements (i.e. Cadmium Sulfide, Zinc Oxide), and composites comprising III-V elements (i.e. Gallium Arsenide, Indium Phosphide).

Through-substrate via 1 facilitate an electrical interconnect between anterior and posterior surfaces of a semiconductor substrate 10. The through-substrate vias 1 are comprised of a doped or intrinsically conducting species of the Group IV, Group VI semiconductor elements or binary semiconductor compounds comprising the II-VI and III-V elements. Optionally the through-substrate vias 1 may be comprised of a metal or metal alloy. In the case that the substrate 10 is comprised of silicon, this is also referred to as a through-silicon via 1.

Stud bumps/solder balls/epoxy 23 facilitate an electrical interconnect between two disparate substrates (silicon 10, PCB 35, or combination of the two).

Bond wire 50 facilitates an electrical interconnect between two disparate substrates (silicon 10, PCB 35, or combination of the two). The bond wire 50 is preferably comprised of a metal or metal alloy.

Figure 1A:
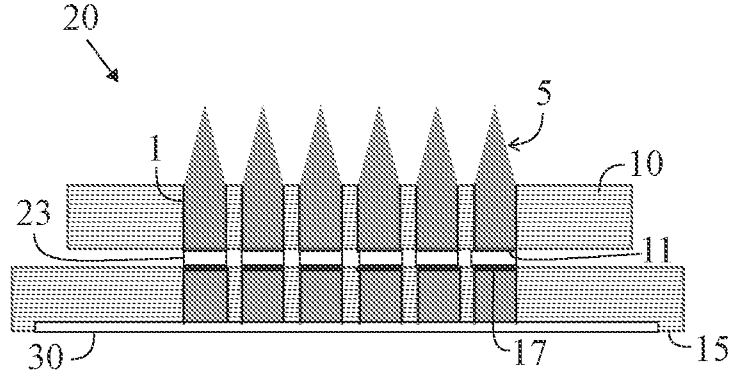
FIG. 1A is a diagrammatic representation of a die stack with CMOS circuitry on posterior surface of a second die.
Figure 1B:
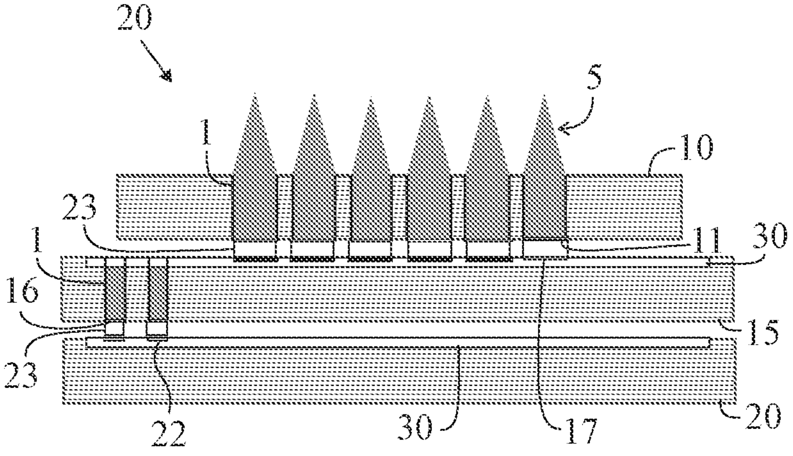
FIG. 1B is a diagrammatic representation of a die stack with CMOS circuitry on anterior surface of a second die and a third die.
Figure 1C:
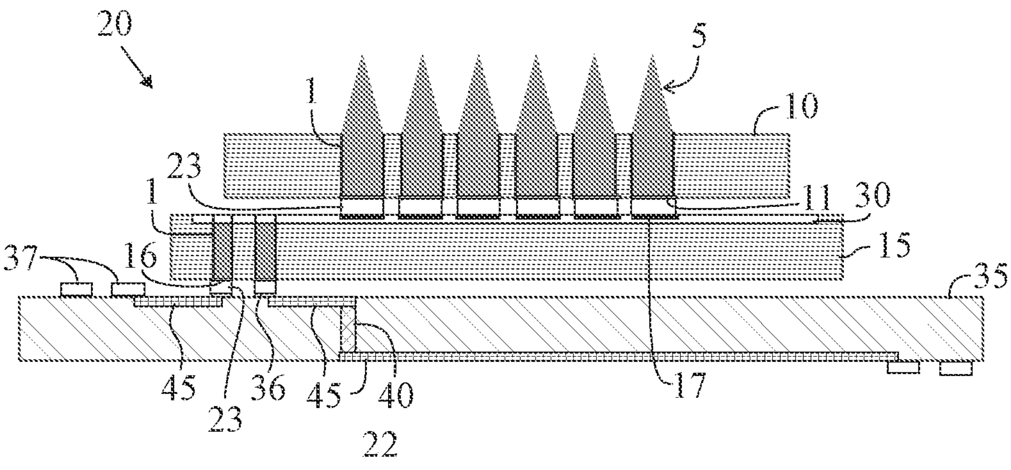
FIG. 1C is a diagrammatic representation of a die stack mounted on a printed circuit board containing assorted electrical circuit components, with CMOS circuitry on anterior surface of a second die.
Figure 1D:
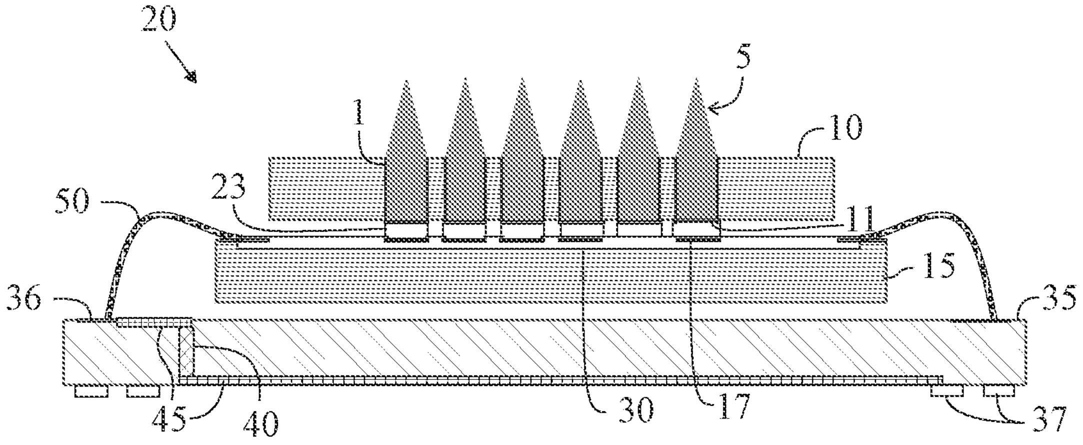
FIG. 1D is a diagrammatic representation of a die stack mounted on a printed circuit board containing assorted electrical circuit components, with CMOS circuitry on anterior surface of a second die.
Figure 1E:
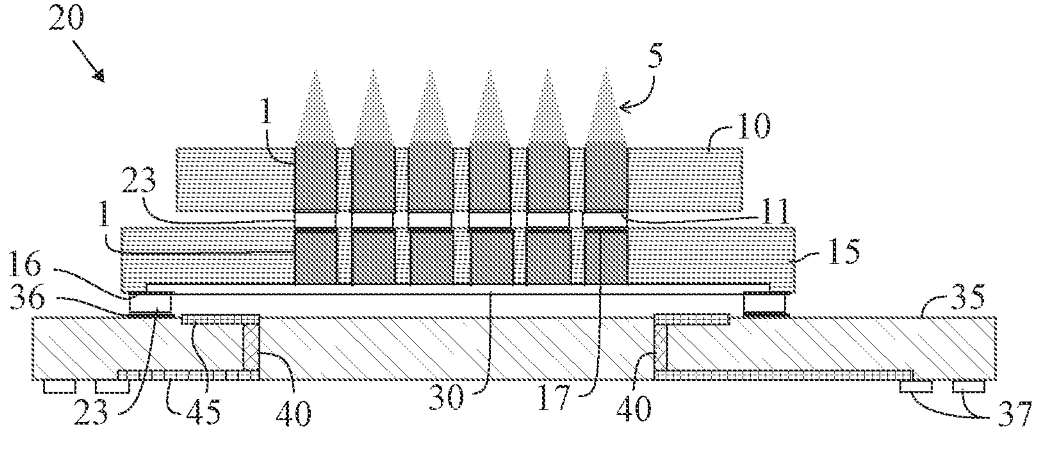
FIG. 1E is a diagrammatic representation of a die stack mounted on a printed circuit board containing assorted electrical circuit components, with CMOS circuitry on posterior surface of a second die.

FIGS. 1-1E illustrate diagrammatic representations of various die-stacking devices 20 that achieve heterogeneous integration of silicon-fabricated solid microneedle sensors and CMOS circuitry. FIG. 1 illustrates a skin-adorned physiological or biochemical sensing device 20 with a first die stack 10 with a CMOS circuitry 30 on an anterior surface of a second die 15. Each of the microneedles 5 is on a posterior pad 11 with stud bumps/sold balls/conductive epoxy 23 between the posterior pads 11 and anterior pads 17. FIG. 1A illustrates a first die stack 10 with CMOS circuitry 30 on posterior surface of second die 15, enabled by the presence of through-substrate vias 1. FIG. 1B illustrates a first die stack 10 with CMOS circuitry 30 on an anterior surface of a second die 15 and a third die 20, enabled by the presence of through-substrate vias 1 on the second die 15. FIG. 1C illustrates a first die stack 10, mounted on a printed circuit board ("PCB") 35 containing assorted electrical circuit components, with CMOS circuitry 30 on an anterior surface of a second die 15, enabled by the presence of through-substrate vias 1 on the second die 15. FIG. 1D illustrates a first die stack 10, mounted on a PCB 35 containing assorted electrical circuit components, with CMOS circuitry 30 on anterior surface of a second die 15, enabled by the presence of wire bonds 50 on the second die 15. FIG. 1E illustrates a die stack, mounted on a PCB 35 which comprises electrical circuit components 37 such as a potentiostat, an analog front end, an amplifier, a filter, an analog-to-digital converter, microcontroller, and a wireless radio, with CMOS circuitry 30 on a posterior surface of the second die 15, enabled by the presence of through-substrate vias 1 on both the second die 15 and PCB 35, and through anterior conductive pads 36 on the PCB 35, which are connected to posterior conductive pads 16 of the second die 15. A TSV 40 through the PCB 35 enables the connection to the electrical components 37 located on the posterior surface of the PCB 35.

Figure 2:
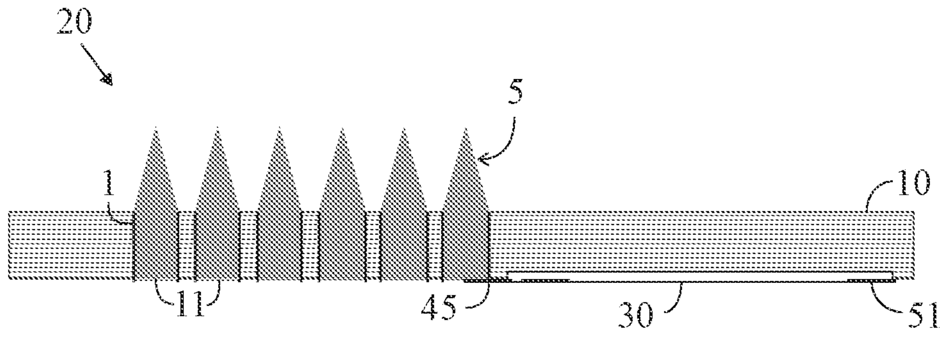
FIG. 2 illustrates microneedles on an anterior surface of die and CMOS circuitry on posterior surface of the die.
Figure 2A:
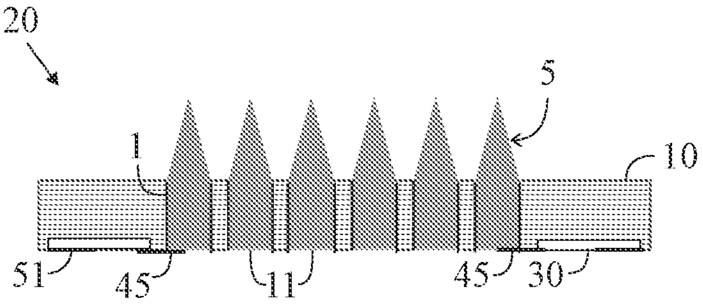
FIG. 2A illustrates microneedles on an anterior surface of die and CMOS circuitry on posterior surface of the die.
Figure 2B:
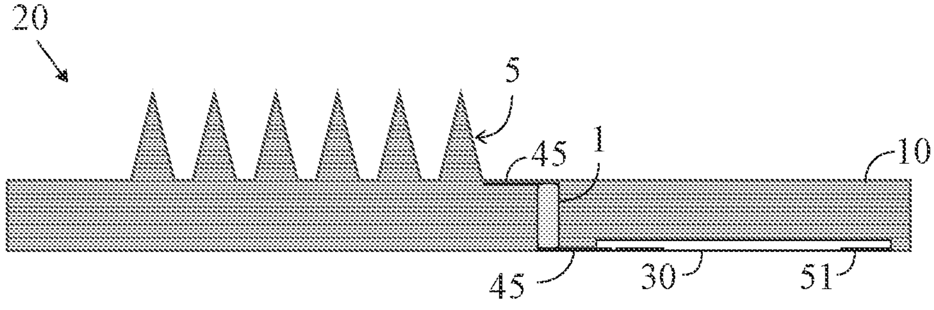
FIG. 2B illustrates microneedles on an anterior surface of die and CMOS circuitry on posterior surface of said die.
Figure 2C:
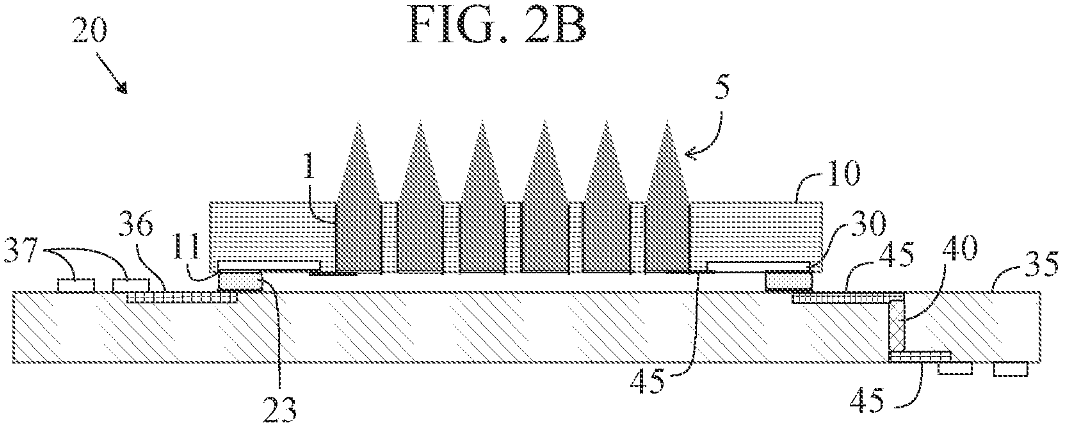
FIG. 2C illustrates microneedles on an anterior surface of die and CMOS circuitry on posterior surface of said die.

FIGS. 2-2C illustrate diagrammatic representations of various co-substrate devices 20 that achieve heterogeneous integration of silicon-fabricated solid microneedle sensors and CMOS circuitry. As shown in FIGS. 2 and 2A, microneedles 5 are positioned on an anterior surface of die 10 with CMOS circuitry 30 on a posterior surface of the die 10, and an interconnect between the microneedles 5 and the CMOS circuitry 30 is enabled by the presence of through-substrate vias 1 positioned colinearly with the microneedles 5 and a conductive trace 45. A bonding pad 51 is positioned on the CMOS circuitry 30. Posterior pads 11 are positioned below the microneedles 5. As shown in FIG. 2B, microneedles 5 are positioned on an anterior surface of a die 10 with CMOS circuitry 30 on a posterior surface of the die 10, and an interconnect is enabled by the presence of through-substrate vias 1 positioned in a spatially distinct region from the microneedles 5. As shown in FIG. 2C, the microneedles 5 are positioned on an anterior surface of a die 10 with CMOS circuitry 30 on a posterior surface of the die 10, and an interconnect is enabled by the presence of through-substrate vias 1 positioned colinearly with the microneedles 5, and the die 10 is mounted on a PCB 35 which comprises electrical circuit components 37 such as a potentiostat, an analog front end, an amplifier, a filter, an analog-to-digital converter, microcontroller, and a wireless radio, with an electrical interconnect achieved between the die 10 and the PCB 35 by means of stud bumps 23, solder balls 23, and/or conductive epoxy 23, and with an anterior conductive pad 36. A TSV 40 connects traces 45 on the anterior surface and posterior surface of the PCB 35.

Figure 3:
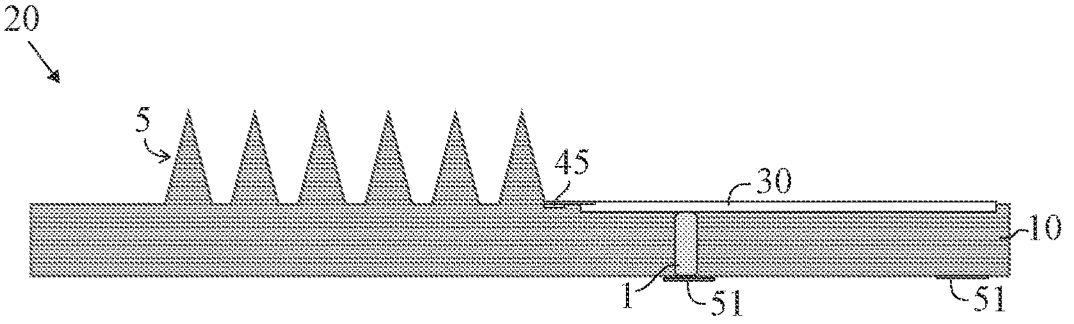
FIG. 3 illustrates microneedles and CMOS circuitry co-located on an anterior surface of die in spatially distinct regions.
Figure 3A:
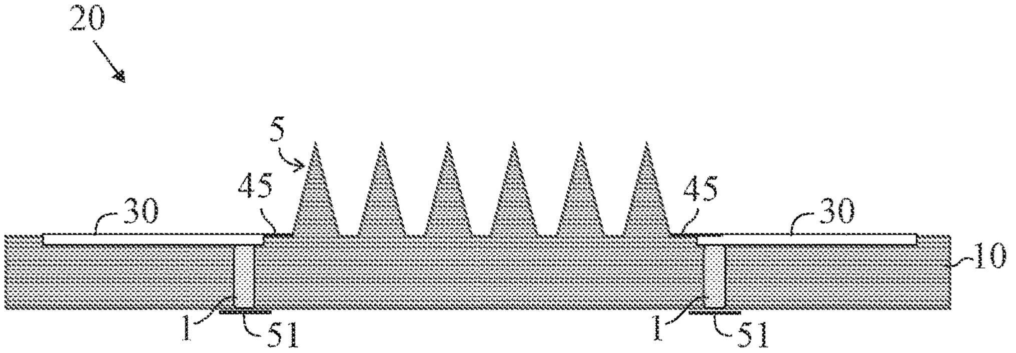
FIG. 3A illustrates microneedles and CMOS circuitry co-located on an anterior surface of die in spatially distinct regions.
Figure 3B:
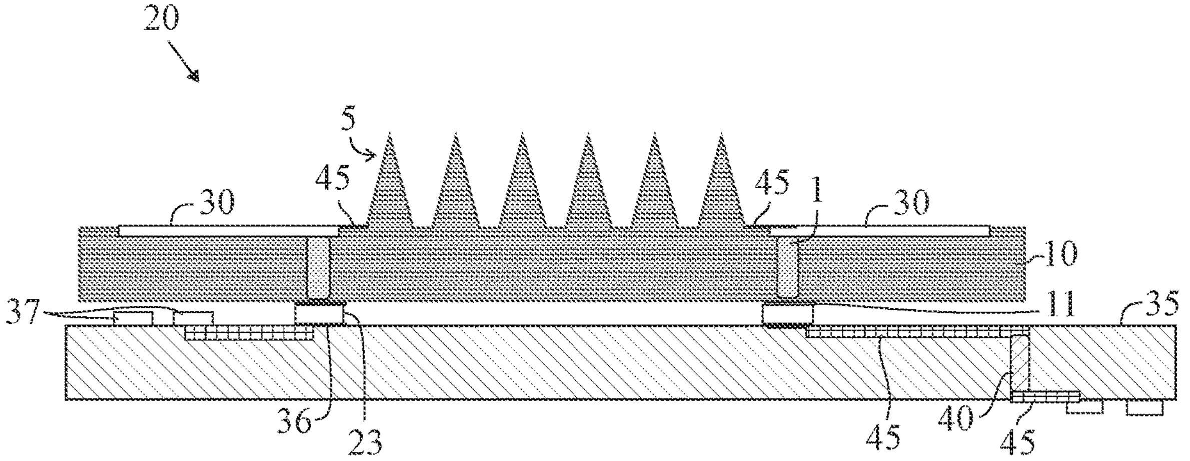
FIG. 3B illustrates microneedles and CMOS circuitry co-located on an anterior surface of die in spatially distinct regions.

FIGS. 3-3B illustrate diagrammatic representations of various co-planar devices 20 that achieve heterogeneous integration of silicon-fabricated solid microneedle sensors and CMOS circuitry. As shown in FIGS. 3 and 3A, microneedles 5 and CMOS circuitry 30 are co-located on an anterior surface of a die 10 in spatially distinct regions, and interconnects between the microneedles 5 and the CMOS circuitry 30 are enabled by the presence of conductive traces 45 positioned co-planarly with the CMOS circuitry 30. Anterior bonding pads 51 are on an anterior surface of the die 10. A TSV 1 connects the CMOS circuitry 30 to the anterior bonding pad 51. As shown in FIG. 3B, microneedles 5 and CMOS circuitry 30 are co-located on an anterior surface of a die 10 in spatially distinct regions, and interconnects between the microneedles 5 and the CMOS circuitry 30 are enabled by the presence of conductive traces 45 positioned co-planarly with the CMOS circuitry 30. The die 10 is mounted on a PCB 35 which comprises electrical circuit components 37 such as a potentiostat, an analog front end, an amplifier, a filter, an analog-to-digital converter, microcontroller, and a wireless radio. An electrical interconnect is achieved between the die 10 and the PCB 35 by means of through-substrate vias 1 in conjunction with stud bumps 23, solder balls 23, and/or conductive epoxy 23, and with an anterior conductive pad 36. A TSV 40 connects traces 45 on the anterior surface and posterior surface of the PCB 35.

One embodiment is a skin-adorned physiological or biochemical sensing device 20. The device 20 comprises a first substrate 10 and a second substrate 15. The first substrate 10 comprises an anterior surface and a posterior surface. The first substrate 10 comprises an array of solid microneedles 5 on the anterior surface designed to penetrate a biological interface to access a physiological fluid or tissue. Each microneedle 5 contains an addressable metal electrode located on the surface of the microneedle 5 which is in electrical communication with a metal surface located on the posterior surface of the first substrate 10 by means of a conductive conduit 1, to form a microneedle sensor component 5 capable of electrical interface with the physiological fluid or tissue. The conductive conduit 1 preferably comprises at least one of a through-substrate via 1. The through-substrate via 1 is preferably comprised of a doped or intrinsically conducting semiconductor; said semiconductor includes at least one of silicon, germanium, silicon germanium, gallium arsenide, indium phosphide, gallium nitride, zinc oxide, and cadmium selenide. The second substrate 15 has an anterior and a posterior surface. The second substrate 15 comprises integrated circuitry 30 on the anterior surface designed to transduce at least one signal produced by an electrophysiological or electrochemical reaction occurring at the metal electrode, to form a transducer component. The posterior surface of the first substrate 10 is stacked to the anterior surface of the second substrate 15. The first substrate 10 is bonded to the second substrate 15 to create an electrical interconnect between the first substrate 10 and the second substrate 15. A sensing device 20 is formed that is capable of interpreting the signal arising from the electrophysiological or electrochemical reaction to ascertain the level of some physiological or biochemical entity.

The first substrate is preferably a semiconductor that includes at least one of silicon, germanium, silicon germanium, gallium arsenide, indium phosphide, gallium nitride, zinc oxide, and cadmium selenide.

The electrical interface preferably includes at least one of applying an electrical stimulus to said physiological fluid or tissue and detecting an electrical signal arising within said physiological fluid or tissue. The electrical stimulus includes at least one of a DC voltage, DC current, AC voltage, AC current, frequency-modulated signal, amplitude-modulated signal, or phase-modulated signal. The electrical signal includes at least one of a DC voltage, DC current, AC voltage, AC current, frequency-modulated signal, amplitude-modulated signal, or phase-modulated signal.

The integrated circuitry 30 preferably comprises at least one of a potentiostat, an analog front end, an amplifier, a filter, an analog-to-digital converter, microcontroller, and a wireless radio.

The bonding means is at least one of stud bumps, solder balls, direct bonding, surface activated bonding, plasma activated bonding, fusion bonding, metal layer bonding, anodic bonding, eutectic bonding, glass frit bonding, insulating layer bonding, adhesive bonding, thermocompression bonding, reactive bonding, transient liquid phase diffusion bonding, physical bonding, and chemical bonding.

The second substrate 15 is further attached to a PCB 35 by means of at least one of: wire bonds 50, stud bumps 23, and solder balls 23.

The PCB 35 preferably comprises discrete electrical or electronic devices such as, but not limited to, batteries, antennas, resistors, capacitors, inductors, diodes, transistors, and discrete semiconductor components.

McCanna et al., U.S. patent application Ser. No. 14/843,926, filed on Sep. 2, 2015, for a Miniaturized Sub-Nano-ampere Sensitivity Low-Noise Potentiostat System is hereby incorporated by reference in its entirety.

Windmiller et al., U.S. patent application Ser. No. 14/955,850, filed on Dec. 1, 2015, for a Method And Apparatus For Determining Body Fluid Loss is hereby incorporated by reference in its entirety.

Windmiller, U.S. patent application Ser. No. 15/177,289, filed on Jun. 8, 2016, for a Methods And Apparatus For Interfacing A Microneedle-Based Electrochemical Biosensor With An External Wireless Readout Device is hereby incorporated by reference in its entirety.

Wang et al., U.S. Patent Publication Number 20140336487 for a Microneedle Arrays For Biosensing And Drug Delivery is hereby incorporated by reference in its entirety.

Windmiller, U.S. patent application Ser. No. 15/590,105 for a Tissue-Penetrating Electrochemical Sensor Featuring A Co Electrodeposited Thin Film Comprised Of A Polymer And Bio-Recognition Element is hereby incorporated by reference in its entirety.

Windmiller, et al., U.S. patent application Ser. No. 15/913,709, filed on Mar. 6, 2018, for Methods For Achieving An Isolated Electrical Interface Between An Anterior Surface Of A Microneedle Structure And A Posterior Surface Of A Support Structure is hereby incorporated by reference in its entirety.

PCT Application Number PCT/US17/55314 for an Electro-Deposited Conducting Polymers For The Realization Of Solid-State Reference Electrodes For Use In Intracutaneous And Subcutaneous Analyte-selective Sensors is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A skin-adorned sensing device, comprising:

a substrate having an anterior surface and a posterior surface;

an array of microneedles configured to sense an electrophysiological reaction or an electrochemical reaction within physiological fluid or tissue, wherein each microneedle of the array of microneedles extends from the anterior surface of the substrate and comprises an addressable electrode located on a surface of the microneedle;

an array of conducting channels extending through the substrate from the anterior surface to the posterior surface, wherein each conducting channel of the array of conducting channels aligns with a corresponding microneedle of the array of microneedles;

semiconductor CMOS circuitry integrated on the posterior surface of the substrate; and a conductive trace positioned on the posterior surface of the substrate and configured to connect the array of conducting channels to the semiconductor CMOS circuitry, wherein the semiconductor CMOS circuitry is configured to interpret a signal produced by the electrophysiological reaction or the electrochemical reaction occurring at the array of microneedles to determine a level of a physiological or biochemical entity.

2. The skin-adorned sensing device of claim 1, wherein the semiconductor CMOS circuitry comprises at least one of a potentiostat, an analog front end, an amplifier, a filter, an analog-to-digital converter, a microcontroller, and a wireless radio.

3. The skin-adorned sensing device of claim 1, wherein the semiconductor CMOS circuitry is patterned on the posterior surface of the substrate.

4. The skin-adorned sensing device of claim 1, wherein the semiconductor CMOS circuitry is configured to interface with a display to present information related to the level of the physiological or biochemical entity.

5. The skin-adorned sensing device of claim 1, wherein the semiconductor CMOS circuitry is positioned on a portion of the substrate that is offset from the array of conducting channels.

6. The skin-adorned sensing device of claim 1, wherein the posterior surface of the substrate is bonded to a second substrate.

7. The skin-adorned sensing device of claim 6, wherein the second substrate comprises a printed circuit board.

8. The skin-adorned sensing device of claim 6, wherein the second substrate is connected to a printed circuit board.

9. The skin-adorned sensing device of claim 6, wherein the semiconductor CMOS circuitry is connected to electrical components on the second substrate through a conductive interface between the semiconductor CMOS circuitry and the second substrate.

10. The skin-adorned sensing device of claim 9, wherein the electrical components are positioned on an anterior surface and a posterior surface of the second substrate, the anterior surface and the posterior surface connected through a conductive channel.

11. The skin-adorned sensing device of claim 1, wherein the array of microneedles is configured to penetrate a user's skin to access the physiological fluid or tissue.

12. A skin-adorned sensing device, comprising:

a substrate having an anterior surface and a posterior surface;

an array of microneedles configured to sense an electrophysiological reaction or an electrochemical reaction within physiological fluid or tissue, wherein each microneedle of the array of microneedles extends from the anterior surface of the substrate and comprises an addressable electrode located on a surface of the microneedle;

at least one conducting channel extending through the substrate from the anterior surface to the posterior surface;

semiconductor CMOS circuitry integrated on the posterior surface of the substrate; and at least one conductive trace positioned on the substrate and configured to connect the array of microneedles to the semiconductor CMOS circuitry via the at least one conducting channel, wherein the semiconductor CMOS circuitry is configured to interpret a signal produced by the electrophysiological reaction or the electrochemical reaction occurring at the array of microneedles to determine a level of a physiological or biochemical entity.

13. The skin-adorned sensing device of claim 12, wherein the semiconductor CMOS circuitry comprises at least one of a potentiostat, an analog front end, an amplifier, a filter, an analog-to-digital converter, a microcontroller, and a wireless radio.

14. The skin-adorned sensing device of claim 12, wherein the semiconductor CMOS circuitry is patterned on the posterior surface of the substrate.

15. The skin-adorned sensing device of claim 12, wherein a first conductive trace is positioned on the anterior surface of the substrate and is configured to connect the array of microneedles to a portion of the at least one conducting channel at the anterior surface of the substrate, and wherein a second conductive trace is positioned on the posterior surface of the substrate and is configured to connect a portion of the at least one conducting channel at the posterior surface of the substrate to the semiconductor CMOS circuitry.

16. The skin-adorned sensing device of claim 12, wherein the semiconductor CMOS circuitry is positioned on a portion of the substrate that is offset from the array of microneedles.

17. The skin-adorned sensing device of claim 12, wherein the posterior surface of the substrate is bonded to a second substrate.

18. The skin-adorned sensing device of claim 17, wherein the second substrate comprises a printed circuit board.

19. The skin-adorned sensing device of claim 17, wherein the second substrate is connected to a printed circuit board.

20. A method for quantifying a physiological or biochemical entity in a physiological fluid or tissue, the method comprising:

providing a device comprising:

a substrate having an anterior surface and a posterior surface;

an array of microneedles configured to sense an electrophysiological reaction or an electrochemical reaction within physiological fluid or tissue, wherein each microneedle of the array of microneedles extends from the anterior surface of the substrate and comprises an addressable electrode located on a surface of the microneedle;

at least one conducting channel extending through the substrate from the anterior surface to the posterior surface;

semiconductor CMOS circuitry integrated on the posterior surface of the substrate; and at least one conductive trace positioned on the substrate and configured to connect the array of microneedles to the semiconductor CMOS circuitry via the at least one conducting channel;

penetrating a biological interface with the array of microneedles;

routing a signal produced by the electrophysiological or electrochemical reaction within the physiological fluid or tissue from a first microneedle of the array of microneedles to the semiconductor CMOS circuitry via the at least one conducting channel and the at least one conductive trace; and interpreting the signal with the semiconductor CMOS circuitry to determine a level of the physiological or biochemical entity.

* * * * *